(12) United States Patent
Chu et al.

(10) Patent No.: US 9,554,886 B2
(45) Date of Patent: Jan. 31, 2017

(54) MEDICAL ASSEMBLY WITH TACTILE FEEDBACK

(71) Applicant: Boston Scientific Scimed, Inc., Maple Grove, MN (US)

(72) Inventors: Michael S. H. Chu, Brookline, MA (US); Kenneth M. Flynn, Woburn, MA (US); Sharmad S. Joshi, Natick, MA (US); James M. Goddard, Pepperell, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 904 days.

(21) Appl. No.: 13/866,681

(22) Filed: Apr. 19, 2013

(65) Prior Publication Data
US 2013/0282034 A1 Oct. 24, 2013

Related U.S. Application Data

(60) Provisional application No. 61/636,902, filed on Apr. 23, 2012, provisional application No. 61/745,101, filed on Dec. 21, 2012.

(51) Int. Cl.
*A61F 2/02* (2006.01)
*A61F 2/00* (2006.01)
(Continued)

(52) U.S. Cl.
CPC ........... *A61F 2/0063* (2013.01); *A61F 2/0045* (2013.01); *A61B 17/06109* (2013.01);
(Continued)

(58) Field of Classification Search
CPC .... A61F 2/0004; A61F 2/0031; A61F 2/0045; A61F 2/0063; A61F 2002/0068; A61F 2/0072; A61B 17/06109
See application file for complete search history.

(56) References Cited

U.S. PATENT DOCUMENTS

2004/0073234 A1  4/2004 Chu et al.
2005/0043580 A1  2/2005 Watschke et al.
(Continued)

FOREIGN PATENT DOCUMENTS

CN   101027012 A    8/2007
CN   101128163 A    2/2008
(Continued)

OTHER PUBLICATIONS

International Search Report and Written Opinion for PCT Patent Application No. PCT/US2013/037551, mailed Jul. 2, 2013, 10 pages.
(Continued)

*Primary Examiner* — Katherine Rodjom
(74) *Attorney, Agent, or Firm* — Brake Hughes Bellermann LLP

(57) ABSTRACT

The present invention discloses a medical assembly including an implant, a first sleeve, a second sleeve and an elongate member. The implant has a first portion, a second portion and a mid portion. The first portion of the implant is configured to be enclosed by the first sleeve and the second portion of the implant is configured to be enclosed by the second sleeve. The elongate member is configured to couple the implant with the first sleeve and the second sleeve and is configured to respectively extend from the first portion to the mid portion of the implant and past the mid portion such that the elongate member exits the implant through the mid portion and forms a loop near the mid portion.

19 Claims, 29 Drawing Sheets

(51) Int. Cl.
    *A61B 17/06*         (2006.01)
    *A61B 17/00*         (2006.01)

(52) U.S. Cl.
    CPC ..... *A61B 90/90* (2016.02); *A61B 2017/00805* (2013.01); *A61B 2017/0608* (2013.01); *A61F 2250/0007* (2013.01); *A61F 2250/0091* (2013.01); *A61F 2250/0097* (2013.01)

(56) References Cited

U.S. PATENT DOCUMENTS

| | | |
|---|---|---|
| 2005/0177022 A1 | 8/2005 | Chu et al. |
| 2005/0250977 A1 | 11/2005 | Montpetit et al. |
| 2005/0256366 A1 | 11/2005 | Chu |
| 2005/0277807 A1 | 12/2005 | MacLean et al. |
| 2007/0038018 A1 | 2/2007 | Chu |
| 2008/0207988 A1 | 8/2008 | Hanes |
| 2009/0171142 A1 | 7/2009 | Chu |
| 2009/0171143 A1* | 7/2009 | Chu .................. A61B 17/0401 600/37 |
| 2011/0124954 A1 | 5/2011 | Ogdahl et al. |

FOREIGN PATENT DOCUMENTS

| | | |
|---|---|---|
| CN | 101686855 A | 3/2010 |
| CN | 101795640 A | 8/2010 |
| CN | 101801281 A | 8/2010 |
| CN | 102083389 A | 6/2011 |
| JP | 2006517115 A | 7/2006 |
| WO | 2004/016180 A2 | 2/2004 |
| WO | 2008/042433 A1 | 4/2008 |
| WO | 2010/121053 A1 | 10/2010 |
| WO | 2011/026494 A3 | 4/2011 |

OTHER PUBLICATIONS

International Preliminary Report on Patentability for PCT Patent Application No. PCT/US2013/037551, mailed Nov. 6, 2014, 7 pages.
First Examiner Report for Australian Patent Application No. 2013252558, mailed on Nov. 18, 2014, 3 pages.
Office Action for Chinese Patent Application No. 201380021319.6, mailed on Jul. 22, 2015, 8 pages.
Office Action for Canadian Patent Application No. 2,865,196, mailed on Aug. 20, 2015, 4 pages.
Notice of Acceptance for AU Application No. 2013252558, mailed Sep. 18, 2015, 57 pages.
Response to Notice of Acceptance for AU Application No. 2013252558, filed Sep. 16, 2015, 10 pages.
Response to Office Action for Canadian Patent Application No. 2,865,196, filed on Feb. 19, 2016, 6 pages.
Office Action for Chinese Patent Application No. 201380021319.6, mailed on Feb. 26, 2016, 5 pages.
Response Office Action for Chinese Patent Application No. 201380021319.6, filed on May 10, 2016, 5 pages.
Response Office Action for Chinese Patent Application No. 201380021319.6, filed on Dec. 4, 2015, 11 pages.
Notice of Decision to Grant for JP Application No. 2014-561195, mailed Dec. 7, 2015, 3 pages.
Office Action Response for JP Application No. 2014-561195, filed Oct. 26, 2015, 3 pages.

* cited by examiner

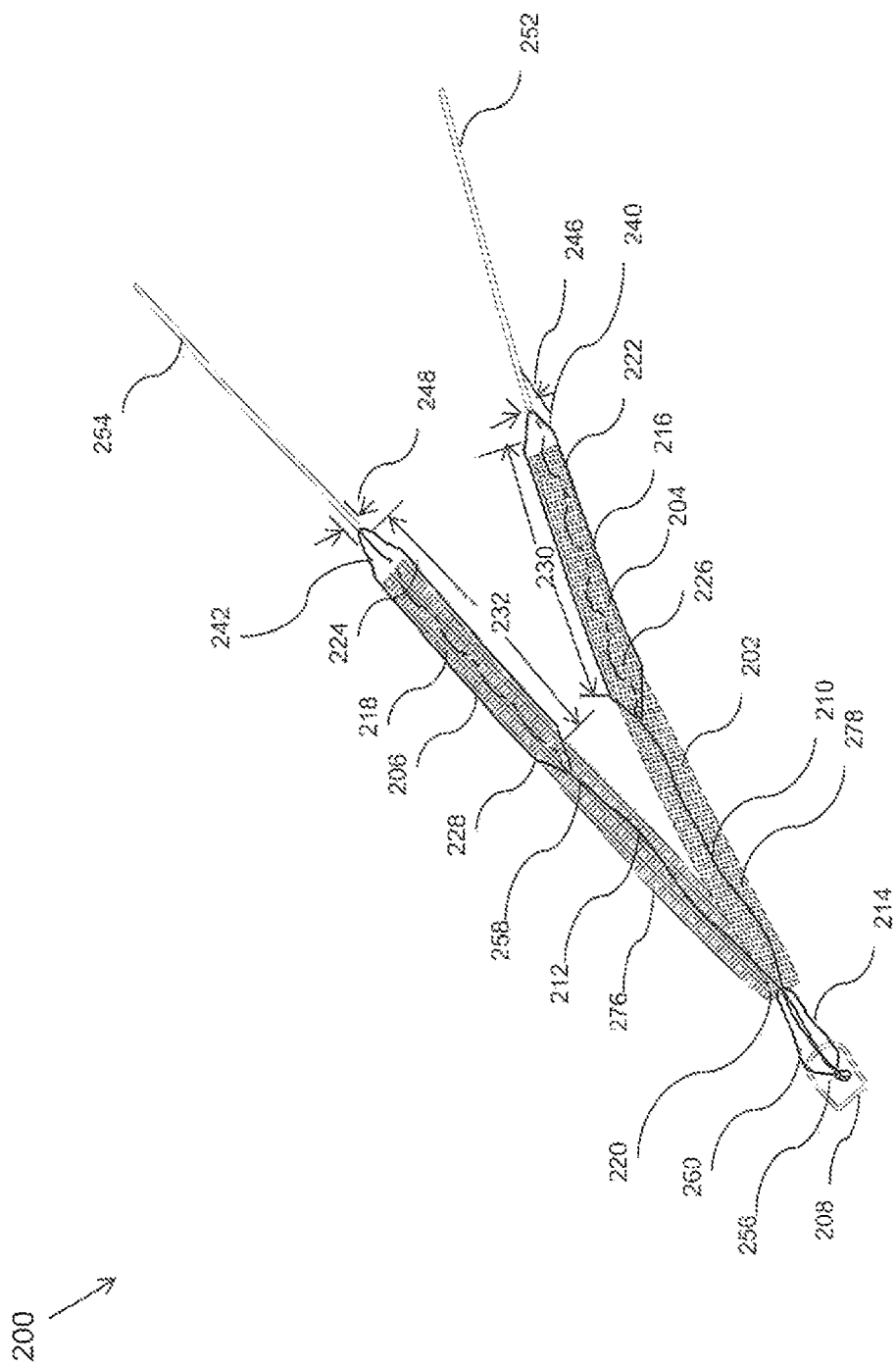

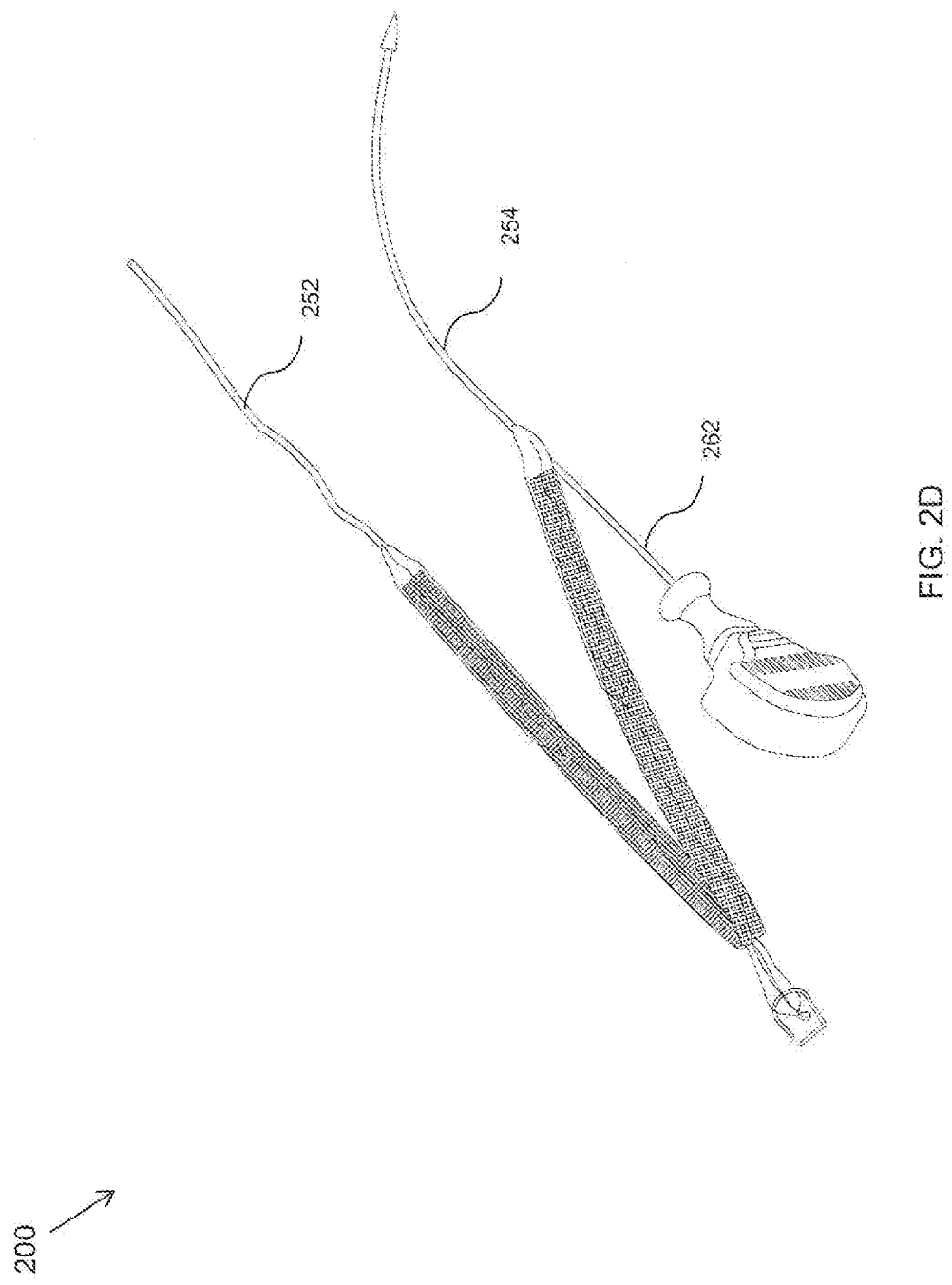

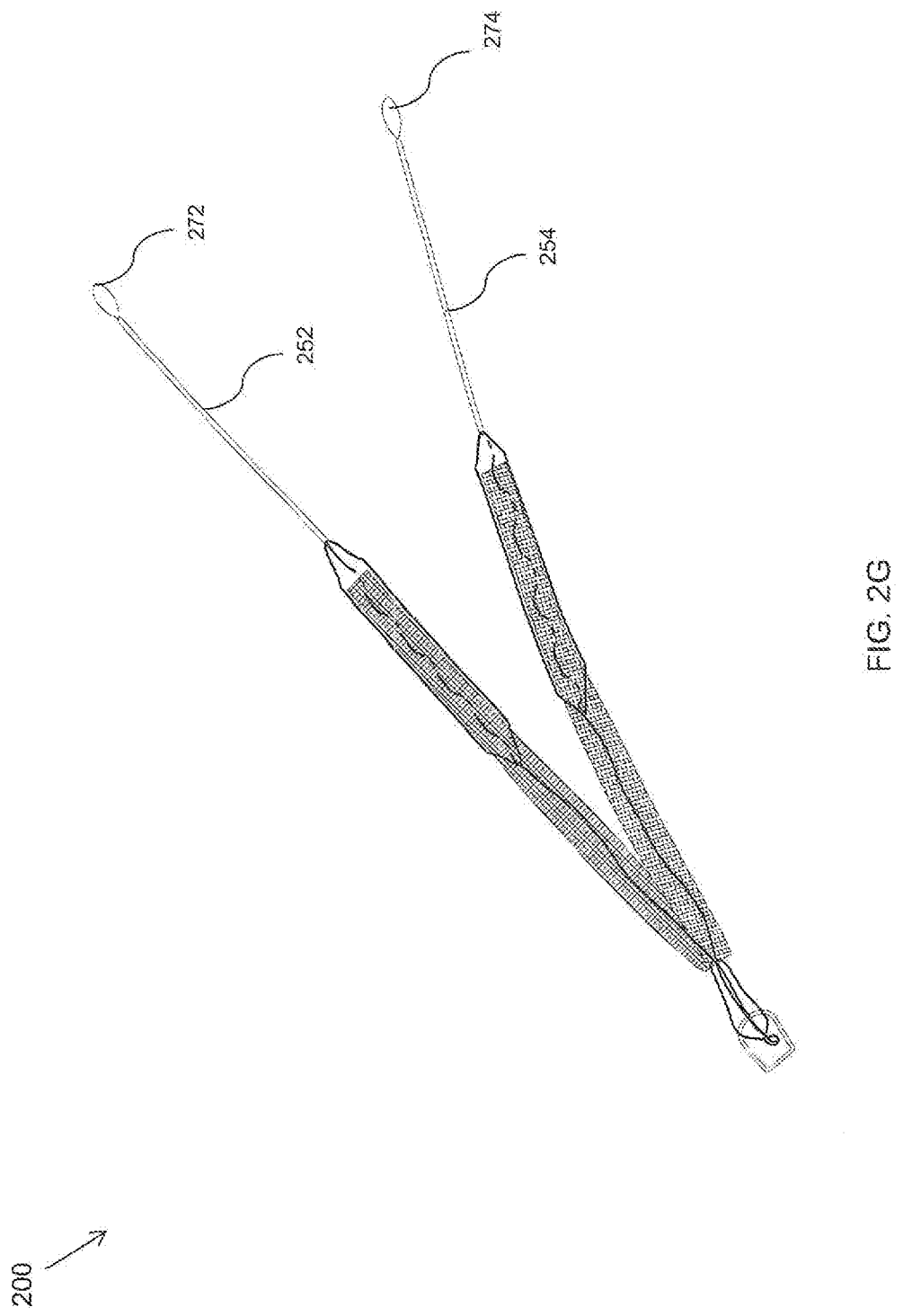

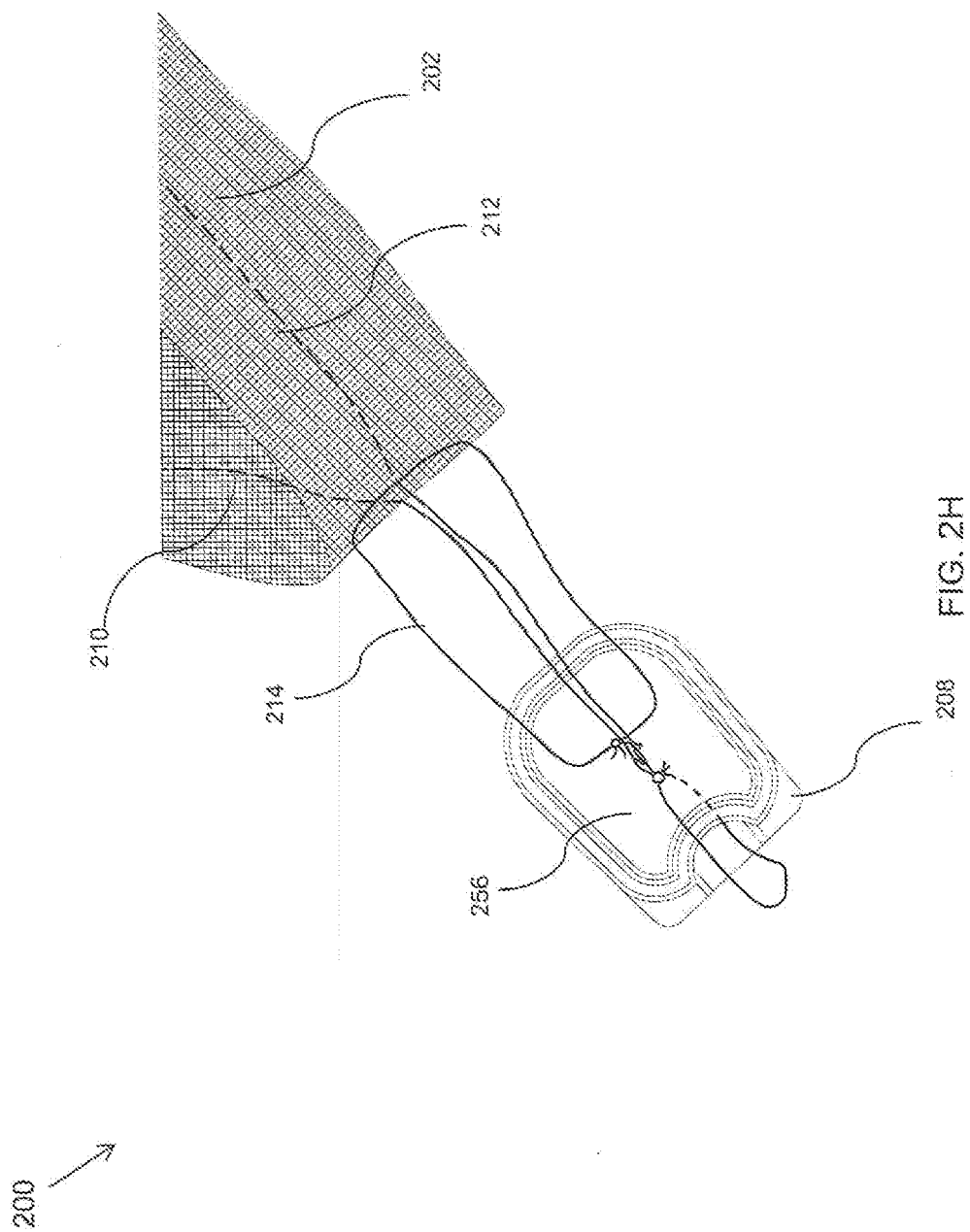

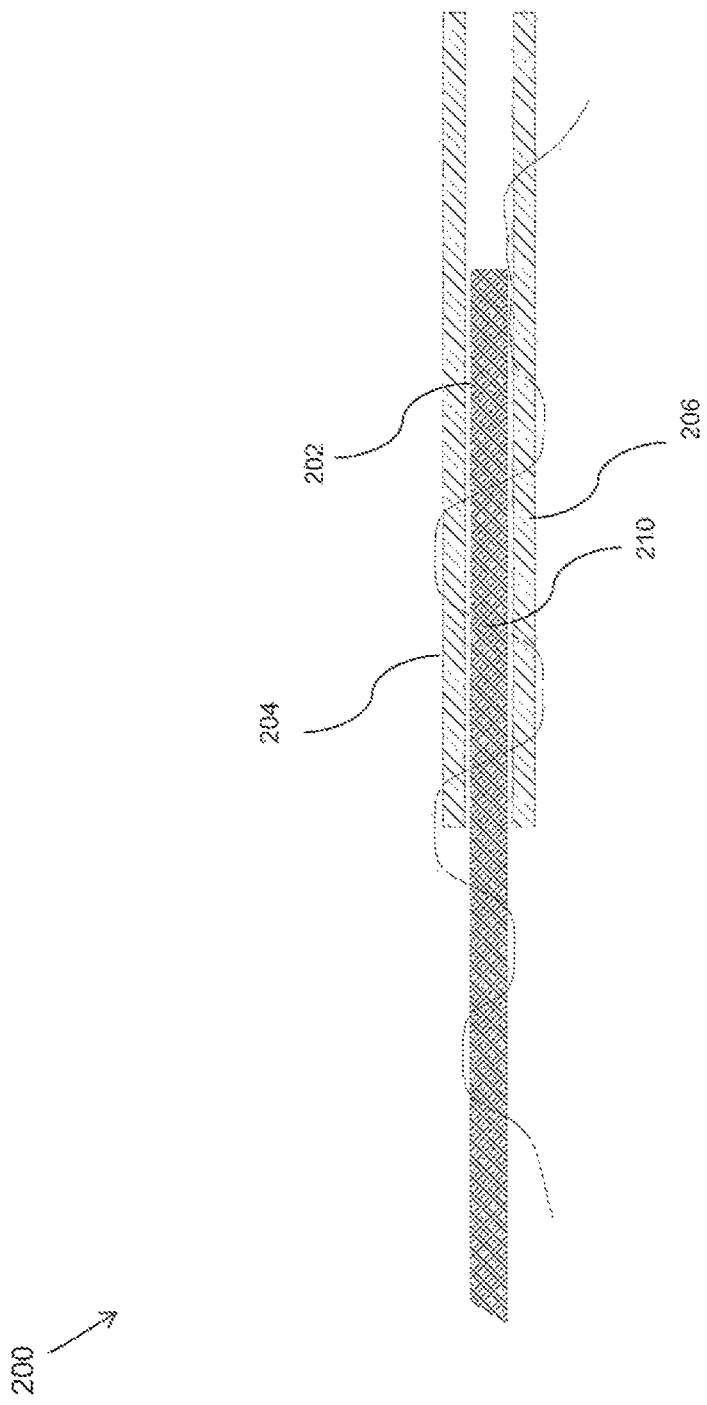

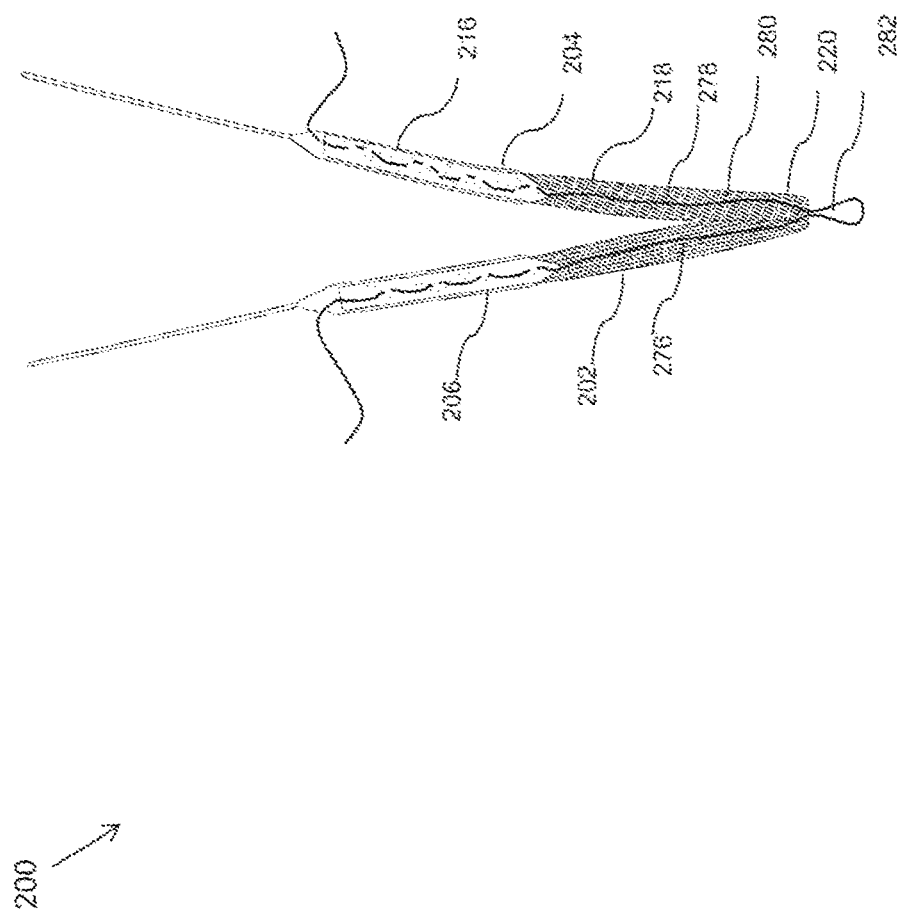

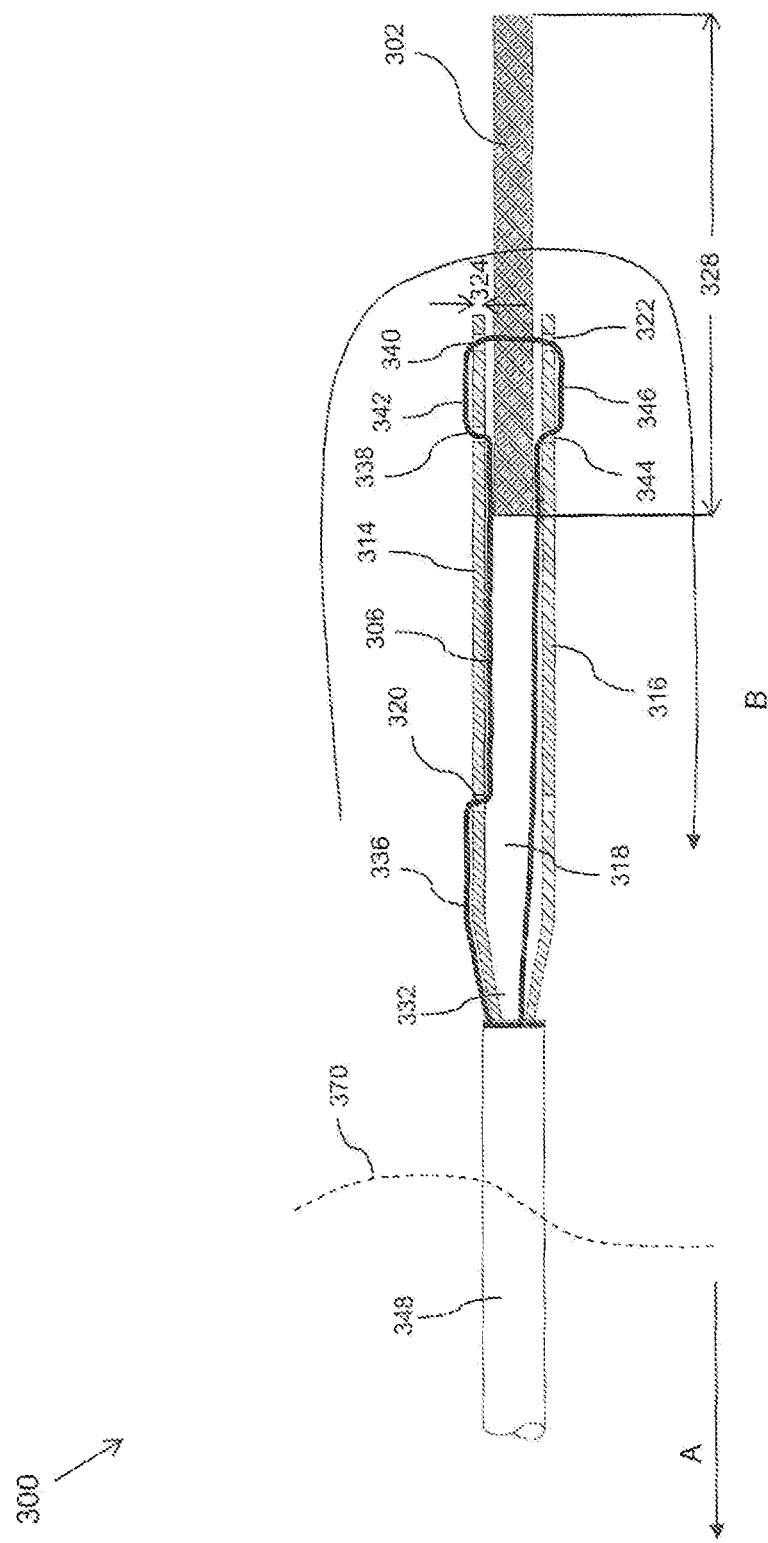

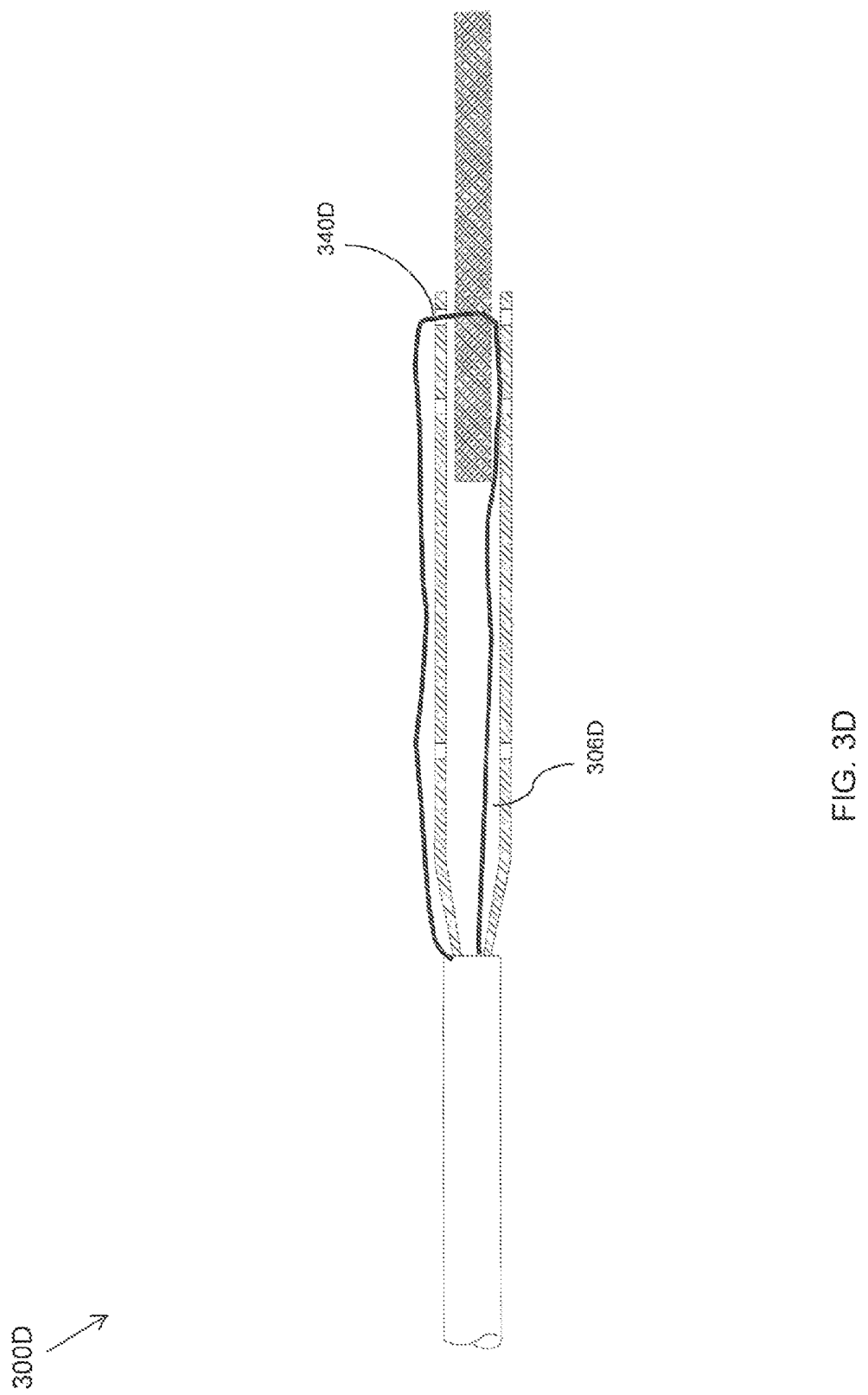

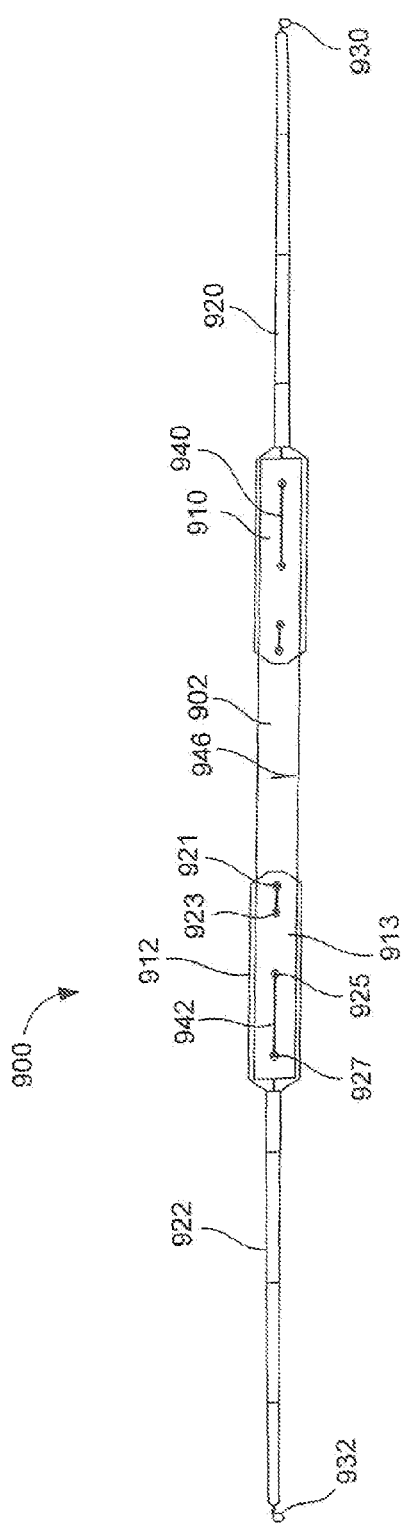
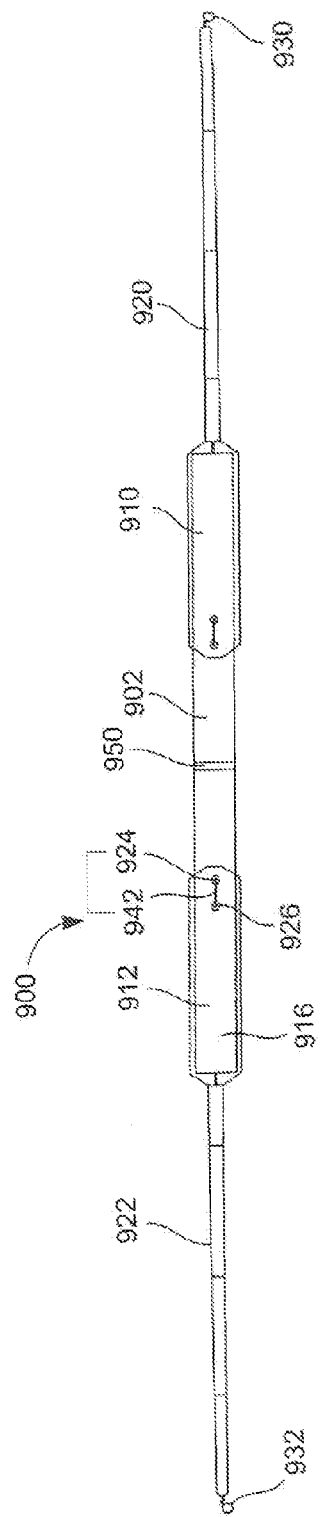
FIG. 3G
FIG. 3H

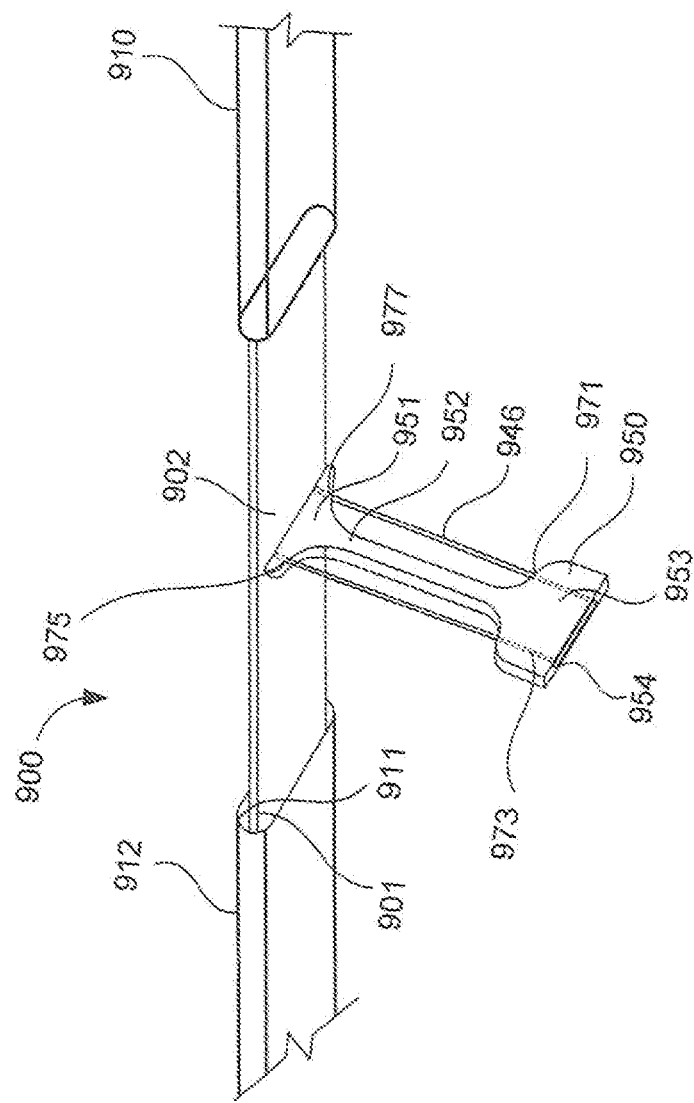

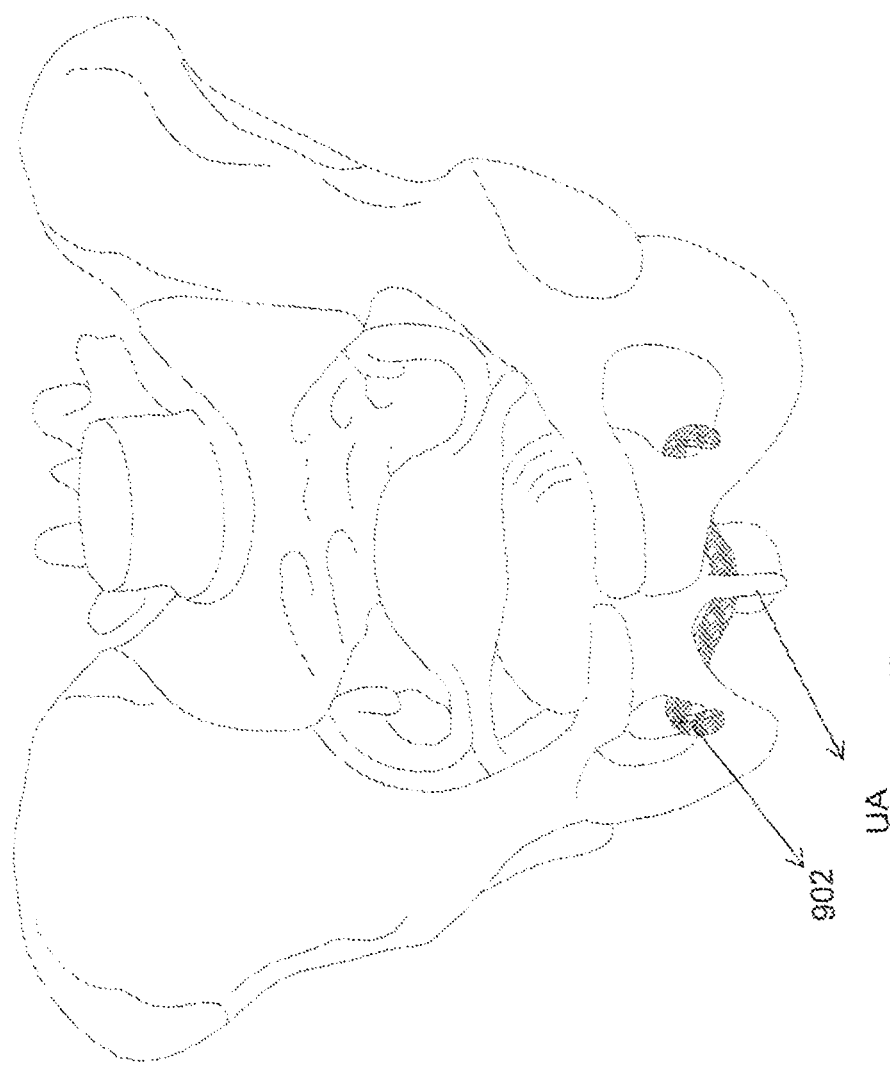

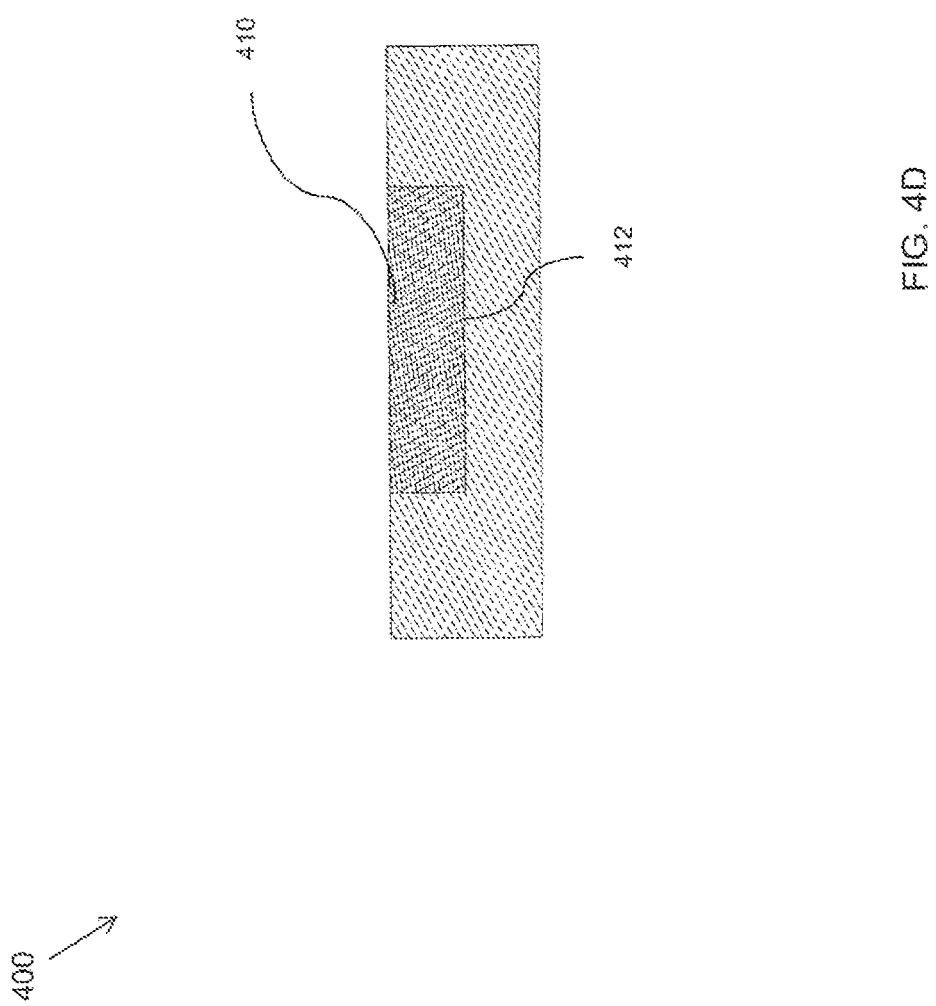

MEDICAL ASSEMBLY WITH TACTILE FEEDBACK

CROSS-REFERENCE TO RELATED APPLICATIONS

This application is a nonprovisional of, and claims priority to, U.S. Patent Application No. 61/745,101, filed on Dec. 21, 2012, entitled "MEDICAL ASSEMBLY WITH TACTILE FEEDBACK", and also claims priority to U.S. Patent Application No. 61/636,902, filed on Apr. 23, 2012, entitled "MEDICAL ASSEMBLY WITH TACTILE FEEDBACK", both of which are incorporated by reference herein in their entirety.

BACKGROUND

Field

The present invention generally relates to surgical devices and procedures, particularly devices and methods for the delivery of implants within a patient's body.

Description of the Related Art

Pelvic health for men and women is a medical area of high importance. Examples of common pelvic ailments include incontinence (e.g. fecal and urinary), pelvic tissue prolapse (e.g. female vaginal prolapse), and other conditions of the pelvic floor.

Many surgical options have been developed for the correction of Urinary Incontinence due to hypermobility and/or Intrinsic Sphincteric Deficiency. One type of surgical procedure found to be a successful treatment option is an implant-based procedure. It involves placement of bodily implants under a bladder neck or a mid-urethra or any other location to provide a support platform.

Some slings or implants for incontinence repair are delivered with long sleeves that cover or enclose the implant and protect bodily tissues. A sleeve can be a single piece sleeve or a two piece sleeve that are attached on contra lateral sides and joined near the midpoint. The tension of the sling is then adjusted based on patient requirements after delivery within the body. In some cases, an additional tension may be inadvertently induced while removal of the sleeves. Since the sling is almost completely enclosed or confined within the single piece or connected sleeve, the sleeve may not allow the sling to stretch properly during adjustment or positioning. This may also not allow the sling to conform to the contour of dissected anatomy to allow the physician to feel or gauge correct positioning or tension of the sling.

Further, some existing sleeves contact the sling over a large surface area. This may result in an increased frictional resistance between the sling material and the sleeve material that opposes pulling of sleeve from the sling during removal. As a result, the frictional resistance may reposition the sling or disturb the sling location or tension. For example, in some cases, the sling may get stretched more than required while in other cases, it may be loosened. And, both the situations may yield in an inappropriate sling placement; and hence, an ineffective or wrong or incorrect treatment.

In view of the above, there is a need of a method and a device that allows removal of the sleeves from the implant without altering the sling tension or location and also provides an operator with an improved visual and tactile feedback to adjust or readjust the implant.

SUMMARY

In an embodiment, the present invention discloses a medical assembly including an implant, a first sleeve, a second sleeve, and a tab. The implant has a first portion, a second portion, and a mid portion between the first portion and the second portion. The first portion of the implant is configured to be enclosed by the first sleeve and the second portion of the implant is configured to be enclosed by the second sleeve. The implant is further coupled to the tab. The medical assembly further includes a first elongate member, a second elongate member, and a third elongate member. The first elongate member is configured to removably couple the implant with the first sleeve such that the first elongate member extends from the first portion to the mid portion of the implant and past the mid portion and exits the implant through the mid portion. The second elongate member is configured to removably couple the implant with the second sleeve such that the second elongate member extends from the second portion to the mid portion of the implant and past the mid portion and exits the implant through the mid portion. The first elongate member and the second elongate member further are coupled to the tab and to each other at the tab. The medical assembly further includes the third elongate member such that the third elongate member is configured to pass through the mid portion of the implant and form a loop configured to couple the mid portion of the implant with the tab.

In another embodiment, the present invention discloses a medical assembly including an implant and a first sleeve and a second sleeve. The implant has a first portion, a second portion and a mid portion between the first portion and the second portion. The first portion of the implant is configured to be enclosed by the first sleeve and the second portion of the implant is configured to be enclosed by the second sleeve. The medical assembly further includes an elongate member configured to removably couple the implant with the first sleeve and the second sleeve. The elongate member extends from the first portion to the mid portion of the implant and past the mid portion such that the elongate member exits the implant through the mid portion and forms a loop near the mid portion. The elongate member is further configured to enter the implant through the mid portion and extend from the mid portion to the second portion of the implant.

In yet another embodiment, the present invention discloses a medical assembly including an implant, a sleeve and an elongate member. The implant has a first portion, a second portion and a mid portion between the first portion and the second portion. The sleeve includes a top layer, a bottom layer, and a lumen defined between the upper layer and the bottom layer, a first hole provided on the top layer and a second hole provided on the bottom layer. The first hole and the second hole are respectively defined along a thickness of the top layer and the bottom layer. The medical assembly further includes the elongate member that is configured to pass through the first hole, along the lumen and the second hole and couple the implant with the sleeve.

In yet some other embodiment, the present invention discloses a method for placing an implant for the treatment of urinary incontinence in a patient's body. The method includes inserting a medical assembly having a bodily implant into a patient's body such that a first end portion and a second end portion of the bodily implant are enclosed in a first sleeve and a second sleeve respectively. The first sleeve is coupled to the implant by an elongate member through frictional resistance. The method further includes placing the implant underneath a urethra of a patient such that a mid portion of the implant is exposed to a bodily tissue. Upon positioning of the implant, the elongate member is pulled outside the patient's body such that a pulling of the elongate member releases the first sleeve from the bodily implant. In some embodiments, the first sleeve is pulled out in a direction substantially different to a direction of pulling the elongate member.

BRIEF DESCRIPTION OF THE FIGURES

The invention and the following detailed description of certain embodiments thereof may be understood with reference to the following figures:

FIGS. 2A-2G are different views of a medical assembly, in accordance with various embodiment of the present invention.

FIG. 2H illustrates an enlarged view of a portion of a medical assembly, in accordance with an embodiment of the present invention.

FIG. 2I is a cross-sectional side view of a portion of a medical assembly, in accordance with an embodiment of the present invention FIG. 2J is a perspective view of a medical assembly, in accordance with an embodiment of the present invention.

FIGS. 3B, 3C, and 3D illustrate front views of a portion of a medical assembly, in accordance with some embodiments of the present invention.

FIG. 3G is a top view of a medical assembly in accordance with an embodiment of the invention.

FIG. 3H is a bottom view of the medical assembly of FIG. 3G.

FIGS. 3I, 3J, and 3K are perspective views of portions of the medical assembly of FIG. 3G.

FIG. 3L is a schematic view of an implant of the medical assembly of FIG. 3G disposed within a body of a patient

FIGS. 4C and 4D illustrate perspective and cross-sectional views respectively of a sleeve with U configuration coupled to an implant, in accordance with an embodiment of the present invention.

DETAILED DESCRIPTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The terms "a" or "an," as used herein, are defined as one or more than one. The term "another," as used herein, is defined as at least a second or more. The terms "including" and/or "having", as used herein, are defined as comprising (i.e., open transition).

The terms proximal and distal described in relation to various medical devices, apparatuses, and components, as discussed in the subsequent text of the present invention, are referred with a point of reference. The point of reference, as used in this description, is a perspective of an operator. The operator may be a surgeon, a physician, a nurse, a doctor, a technician, and the like, who may perform the procedure of surgery through the patient's body orifice or incision as described in the present invention. The term proximal refers to an area that is closest to the operator. The term distal refers to an area that is farthest from the operator. The patient can be a male, a female or any other mammal.

Figure 1:
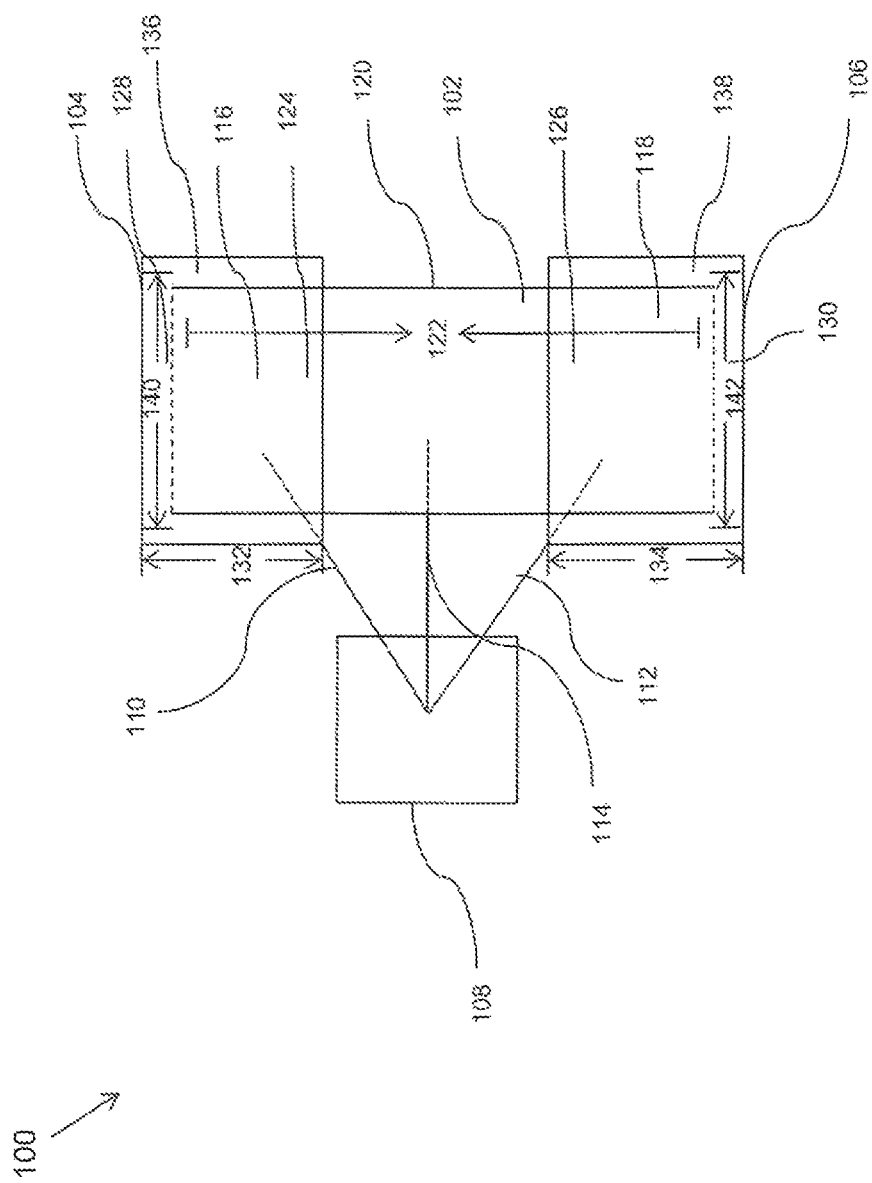
FIG. 1 is a schematic diagram of a medical assembly, in accordance with some embodiments of the present invention.

FIG. 1 is a schematic diagram of a medical assembly 100, in accordance with some embodiments of the present invention. The medical assembly 100 includes an implant 102, a first sleeve 104, a second sleeve 106, a tab 108, a first elongate member 110, a second elongate member 112, and a third elongate member 114.

The implant 102 has a first portion 116, a second portion 118, and a mid portion 120 between the first portion 116 and the second portion 118 with a length 122 of the implant 102, extending between the first portion 116 and the second portion 118 longitudinally. In accordance with various embodiments, the implant 102 can have a variety of shapes such as rectangular, square, trapezoidal, and the like.

In some embodiments, the mid portion of the implant 102 is de-tanged (without tangs). The length of the de-tanged section can vary based on surgical requirements or location of placement inside the patient's body. In some embodiments, the first portion 116 and the second portion 118 may include tangs such that upon placement of the implant 102, the first portion 116 and the second portion 118 of the implant 102 can interact with bodily tissues to help anchor or retain the implant in position within the body of the patient. In some embodiments, the de-tanged section can be made by fusing threads or strands of a mesh edge together by heat. The de-tanged section may, in some embodiments, prevent unraveling of the implant 102 when in tension and thus limits its stretch.

In some embodiments, the implant 102 is made of a synthetic material such as a polymeric material and the like. In some embodiments, the implant 102 includes a polymeric mesh body. The mesh body may comprise a crisscrossed or chain link fence-like design. In such designs, the fibers or strands of the mesh may be woven, linked, or otherwise connected, and may share the stress of a supported load. In other embodiments, the implant 102 includes a polymeric planar body without mesh cells and structures. Exemplary polymeric materials are polypropylene, polyester, polyethylene, nylon, PVC, polystyrene, and the like. In some embodiments, the implant is made of a non-woven polymeric material. In some other embodiments, the implant 102 can be made of natural materials such as biologic material or a cadaveric tissue and the like.

Additionally, in some embodiments, the implant 102 is stretchable and flexible to adapt movements along the anatomy of the human body. In some embodiments, the attributes such as softness, lightness, conformity and strength are required in the implant 102 for efficient tissue repair and implantation. In some embodiments, the implant 102 can be blue in color or any other color that facilitates distinguishing the implant 102 from the sleeves 104 and 106.

As mentioned above, the medical assembly 100 includes the first sleeve 104 configured to enclose the first portion 116 of the implant 102 and the second sleeve 106 configured to enclose the second portion 118 of the implant 102. Each of the first sleeve 104 and the second sleeve 106 includes a proximal end portion 124 and 126 and a distal end portion 128 and 130 with a length 132 and 134 extending between the proximal end portion 124 and 126 and the distal end portion 128 and 130 such that the length 132 of the first sleeve 104 is sufficient to envelop or shield the first portion 116 of the implant and length 134 of the second sleeve 106 is sufficient to shield the second portion 118 of the implant 102. In various embodiments, the first portion 116 is a first end portion of the implant 102 and the second portion 118 is the second end portion of the implant 102 such that the first sleeve 104 and the second sleeve 106 are configured to enclose the first end portion and the second end portion, respectively, of the implant 102. The first sleeve 104 and the second sleeve 106 are together hereafter referred to as sleeves 104 and 106 for simplicity of the description.

In some embodiments, the sleeves 104 and 106 are shaped in the form of hollow tubes or envelopes such that a hollow space within the sleeves 104 and 106 define lumen 136 and 138 therein. The lumen 136 and 138 of the sleeves 104 and 106 are configured to receive the first portion 116 and the second portion 118 that are the first end portion and the second end portion of the implant 102. The first end portion and the second end portion may be respectively disposed within the lumen 136 and 138 of the first sleeve 104 and the second sleeve 106. In some embodiments, the implant 102 may be free-floating within the first sleeve 104 and the second sleeve 106. Alternatively, the implant 102 may be fixed to the sleeves 104 and 106.

The lumen 136 and 138 of the sleeves 104 and 106 have a width 140 and 142 that is larger than the width of the implant 102 at the first and the second end portion 116 and 118 that are configured to be covered by the sleeves 104 and 106. This allows housing of the end portions 116 and 118 of the implant 102 within the lumen 136 and 138 of the sleeves 104 and 106. In some other embodiments, the proximal end portions 124 and 126 of the sleeves 104 and 106 are slightly tapered to facilitate the withdrawal without disrupting the tissues. In some embodiments, the sleeves 104 and 106 can be made of resilient or flexible material such that the width of the lumen 136 and 138 is smaller than the width of the implant 102 in a normal condition. However, in some embodiments, the sleeves 104 and 106 are configured to be stretched due to its flexible material; the width of the lumen 136 and 138 can be increased to an extent that makes the receipt of the implant 102 possible within the lumen 136 and 138.

In some embodiments, the sleeves 104 and 106 are made of polymer and may be colored blue. In other embodiments, the sleeves 104 and 106 can be manufactured from an opaque or a transparent plastic film. The transparent plastic film enables visual examination of the implant 102. The sleeves 104 and 106 can be single or multiple ply. The sleeves 104 and 106 can be made by extruding or sandwiching two sheets of polymer together. In general, the sleeves 104 and 106 may be composed of any biocompatible material known in the art. Such materials may include, for example, polyethylene, PTFE, and EPTFE. The sleeves 104 and 106 may be composed of one material or, in some embodiments, the sleeves 104 and 106 may be made of a multilayered structure composed of one or more materials already mentioned. The sleeves 104 and 106 may be any length or width useful for implanting and positioning the implant 102 within the body of the patient, and may be flexible and easily manipulable when the implant 102 is disposed therein. In various embodiments described herein, the sleeves 104 and 106 may be long enough and wide enough to define the lumen 136 and 138 that is appropriately sized for accepting the first end portion and the second end portion.

As per the various embodiments of the present invention described above, the first portion 116 of the implant 102 enclosed by the first sleeve 104 and the second portion 118 of the implant 102 enclosed by the second sleeve 106 facilitate in a non-binding release or withdrawal of the first sleeve 104 and the second sleeve 106 from the implant 102. The non-binding removal of the sleeves 104 and 106 implies that the sleeves 104 and 106 are held with the implant 102 only through a frictional resistance that is capable to hold them but not large enough to cause any damage to the implant 102 during pulling or removal. This may reduce additional tension that can be induced to the implant 102 as the sleeves 104 and 106 are pulled or released off the implant 102.

In accordance with some embodiments, the sleeves 104 and 106 are configured to enclose the end portions 116 and 118 of the implant 102 such that only a small surface area of the implant 102 comes in contact with the sleeves 104 and 106. In an embodiment of the present invention, the first sleeve 104 and the second sleeve 106 together encloses a maximum of half of a total length 122 of the implant 102. In some embodiments, the first sleeve 104 and the second sleeve 106 together encloses less than half of the total length 122 of the implant 102. In some other embodiments, the first sleeve 104 and the second sleeve 106 together encloses half of the total length 122 of the implant 102. In some other embodiments, the first sleeve 104 and the second sleeve 106 together encloses about half of the total length 122 of the implant 102. In some other embodiments, the first sleeve 104 and the second sleeve 106 may together enclose slightly or substantially more than half of the total length 122 of the implant 102. With a small surface area contact between the implant 102 and the sleeves 104 and 106, the friction between the implant 102 and the sleeves 104 and 106 is less to disrupt the implant tension, leading to a more precise implant placement.

Figure 4A:
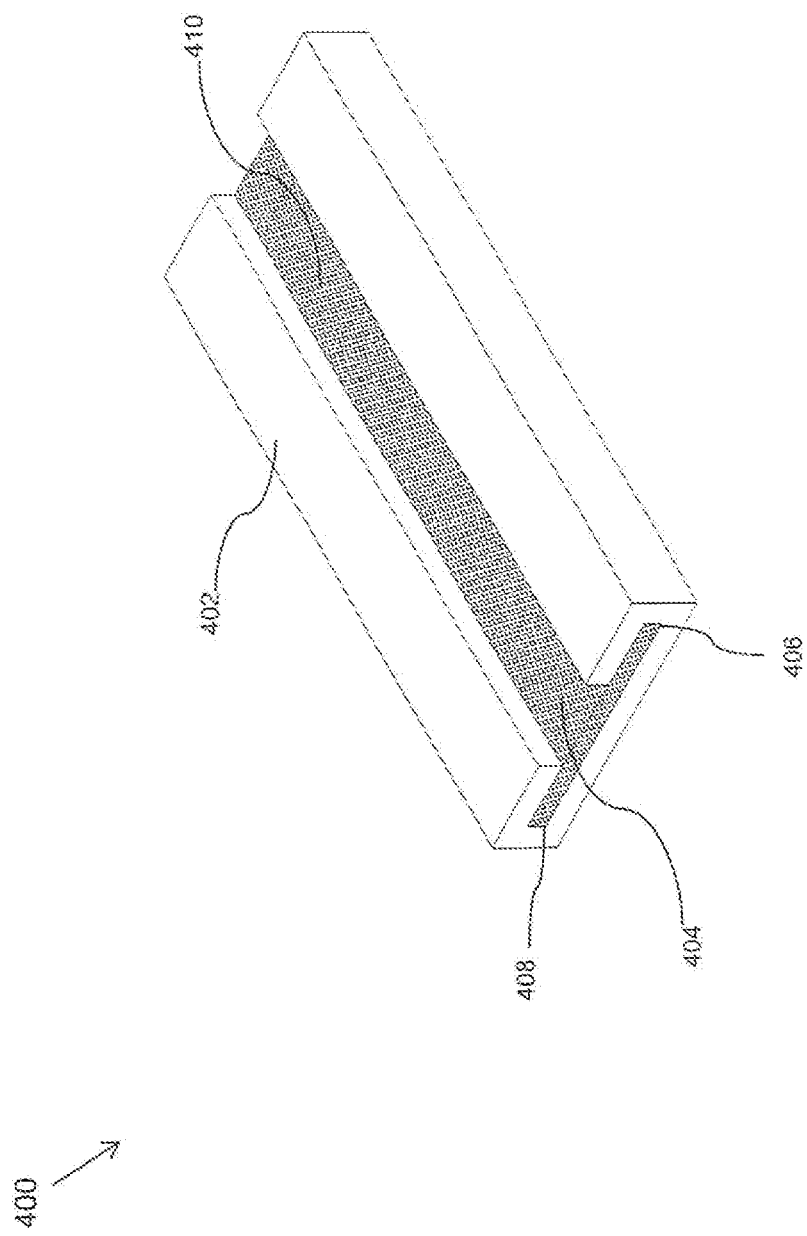
FIGS. 4A and 4B illustrate perspective and cross-sectional views respectively of a sleeve with C configuration coupled to an implant, in accordance with an embodiment of the present invention.
Figure 4B:
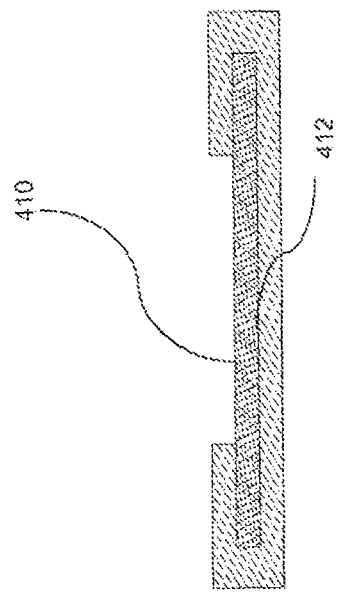
Figure 4B:

In some embodiments, the sleeves 104 and 106 can have a C configuration, as shown in FIGS. 4A and 4B later. In the C configuration, the sleeves 104 and 106 encloses the implant 102 in a manner that a first side (right side), a second side (left side), some portion of a first surface (top surface), and a second surface (bottom surface) of the implant 102 are enclosed, whereas some portion of the first surface (top surface) is exposed to bodily tissues is are not shielded within the sleeves 104 and 106. The "some portion" can be along half of the width of the sleeves 104 and 106, or about half of the width or lesser than half of the width or slightly more than half of the width, and the like as per the requirements. In some other embodiments, the sleeves 104 and 106 can have a U configuration. The U configuration encloses the first side, the second side and the second surface (bottom surface) while the first surface (top surface) of the implant 102 is completely exposed to the bodily tissues and not shielded within the sleeves 104 and 106. The U configuration of the sleeves 104 and 106 is illustrated and described in conjunction with FIGS. 4C and 4D later. The sleeves 104 and 106 may have a slit along its length 132 and 134 in which the implant 102 can be held.

In some embodiments, a distal portion of the sleeves 104 and 106 is configured with a taper and a loop or a hole, dilator, tube, connector or the like to be used to associated to a delivery device. The delivery device is further described later.

In certain embodiments of the present invention, the medical assembly 100 may also include a first dilator configured to be coupled to the first sleeve 104, and a second dilator configured to be coupled to the second sleeve 106. The first dilator and the second dilator are configured to be coupled respectively to the distal ends 128, and 130 of the first sleeve 104 and the second sleeve 106. In some embodiments, the first and the second dilator are further configured to be coupled to a delivery device. The delivery device is a medical instrument that can be used to facilitate delivery of the medical assembly 100 including the implant 102 within the patient's body. A few examples of delivery devices may include the Boston Scientific Corporation Obtryx™, Lynx™, Advantage™, Prefyx™ delivery device or any other delivery device. In some embodiments, the first and second dilators are small in diameter to provide a less invasive surgery. In some embodiments, an association loop can be formed, such as with a thread for an association of the dilators with the delivery device. The association loop is provided at distal ends of the first dilator and the second dilator to associate the first dilator and the second dilator to the delivery device.

As mentioned above, the medical assembly 100 further includes the tab 108 configured to be coupled to the implant 102. The tab 108 is configured to identify the mid portion 120 of the implant. In some embodiments, the tab 108 can be colored for easy visualization during surgical procedure.

The tab 108 is further provided with a slot to receive the first elongate member 110, the second elongate member 112, and the third elongate member 114. In certain embodiments, the first elongate member 110 is configured to removably couple the implant 102 with the first sleeve 104 such that the first elongate member 110 extends from the first portion 116 to the mid portion 120 of the implant 102 and past the mid portion 120 and exits the implant 102 through the mid portion 120. The second elongate member 112 is configured to removably couple the implant 102 with the second sleeve 106 such that the second elongate member 112 extends from the second portion 118 to the mid portion 120 of the implant 102 and past the mid portion 120 and exits the implant 102 through the mid portion 120. The first elongate member 110 and the second elongate member 112 are coupled together at the tab 108 to form a first knot at the tab 108 or in close proximity of the tab 108. The first knot not only couples the tab 108 to the first elongate member 110 and the second elongate member 112, but also the first elongate member 110 and the second elongate member 112 to each other at the tab. The first knot can be considered as a junction where the first elongate member 110, the second elongate member 112 and the tab 108 are contacted or coupled. In some embodiments, the first elongate member 110, second elongate member 112, and the third elongate member can be a rope, suture, filament, thread, and the like.

In some embodiments, the tab 108 may include multiple slots to receive the first elongate member 110, the second elongate member 112, and the third elongate member 114. In some other embodiments, the first elongate member 110 and the second elongate member 112 may be coupled to the tab 108 through various coupling mechanisms and fasteners instead of directly tying them and forming knots. In such embodiments, various coupling mechanism and fasteners such as staples, glue, heat bonding, pins, and the like may be used.

The tab 108 may be made of any material known in the art, such as, for example, polyethylene, PTFE, or EPTFE, and may be of any color, such as blue, to assist the user in viewing the tab 108. The tab 108 may be sized and otherwise configured to assist in positioning a portion of the implant 102 and/or the sleeves 104 and 106 within the body of a patient.

In some embodiments, the first elongate member 110 and the second elongate member 112 include one of a thread, a medical suture, a filament, a rope, and the like. In some embodiments, the first elongate member 110 and the second elongate member 112 have a single suture or thread running along the maximum of half of the total length 122 of the implant 102. In some other embodiments, the first elongate member 110 and the second elongate member 112 have multiple sutures or threads running along the maximum of half of the total length 122 of the implant 102. For example, multiple sutures or threads may be provided for coupling the implant 102 with the sleeves 104 and 106 such that the sutures or threads are placed adjacent to one another for increasing strength of the coupling.

In some embodiments, the first elongate member 110 and the second elongate member 112 couple the implant 102 with the first sleeve 104 and the second sleeve 106 respectively in a manner that the first elongate member 110 and the second elongate member 112 are threaded in and out through the implant 102. Each of the first elongate member 110 and the second elongate member 112 first passes from the first surface of the implant 102 to the second surface and then from second surface to the first surface, thereby forming one stitch. Similarly, this pattern of stitches continues to a certain length of the implant 102 to form multiple stitches in a sequence that may be termed as a running stitch. The running stitch thus refers to a series of stitches that hold the sleeves 104 and 106 and the implant 102 through frictional resistance together. The elongate members 110 and 112 are threaded in and out of the implant 102 and the sleeves 104 and 106 in a manner that the frictional resistance is reached to an extent where suture can keep the sleeves 104 and 106 and the implant 102 coupled together but may allow decoupling of the implant 102 and the sleeves 104 and 106 when the elongate members 110 and 112 are pulled by overcoming the frictional resistance. The stitches may be of varying length, or same length. In accordance with some embodiments, the running stitch may be in the form of a straight line orientation relative to a direction of pull to facilitate removal of the elongate members 110 and 112. In some embodiments, the running stitch may be in the form of a curve or a zigzag pattern instead of a straight line orientation.

In some embodiments, the first elongate member 110 and the second elongate member 112 may have one free end. In certain other embodiments, the first elongate member 110 and the second elongate member 112 may have no free ends such that one end is tied to the tab 108 and the other end is tucked into the sleeves 104 and 106. In certain embodiments, both the first elongate member 110 and the second elongate member 112 may have a free end.

The medical assembly 100 further includes the third elongate member 114 configured to pass through the mid portion 120 of the implant 102 and form a loop such that the loop couples the mid portion 120 of the implant 102 with the tab 108. In some embodiments, the third elongate member 114 is a thread or a suture and the like, which is a part separate from the implant 102 to be removably coupled to the implant and the tab 108 for coupling the tab 108 with the implant 102 through the loop. In other embodiments, the third elongate member 114 can be an integral part of the implant 102 such that the third elongate member 114 is weaved into the implant 102 center and extend from there outside the implant 102 to form the loop that is configured to receive the tab 108 for coupling the tab 108 with the implant 102. The third elongate member 114 is threaded through the mid portion 120 of the implant 102 such that the third elongate member 114 passes through the implant 102 at the mid portion 120 and then form a loop type of structure. In some embodiments, free ends of the third elongate member 114 can be tied together to form a knot referred to as a second knot. In accordance with these embodiments, the third elongate member 114 first passes through the implant mid portion 120 and then through a slot in the tab 108 and then knotted together to couple the tab 108 with the implant 102. This pattern of association of the implant 102 with the tab 108 is configured to disassociate the implant 102 from the tab 108 by cutting the third elongate member 114 or removing the second knot. In certain embodiments, cutting the third elongate member 114 and a mere pulling of the tab 108 is configured to release the first sleeve 104 and the second sleeve 106 from the implant 102.

In accordance with the embodiments described above, the tab 108 is therefore coupled to the third elongate member 114 directly through the second knot, and also to the first elongate member 110 and the second elongate member 112 through the first knot formed at the tab 108. The first knot not only couples the tab 108 to the first elongate member 110 and the second elongate member 112, respectively, but also the first elongate member 110 and the second elongate member 112 to each other at the tab. Therefore, the first elongate member 110 and the second elongate member 112 are together configured to be removed when the tab 108 is pulled after cutting the second knot formed at the tab 108 by the third elongate member 114. In some embodiments, the first elongate member 110 and the second elongate member 112 can be removed by cutting the third elongate member 114 at a location other than the second knot.

In accordance with an embodiment, the first elongate member 110 can be configured to extend from the first dilator to the implant 102 and the first sleeve 104 such that the first elongate member 110 extends externally at some portion of the implant 102 and the first sleeve 104, and pierces through and extends within the first sleeve 104 and the implant 102 at some other portion. In accordance with these embodiments of threading, the first elongate member 110 may extend from the dilator to and along the first sleeve 104 and the first portion of the implant 102 and then may traverse back toward the first dilator thereby forming a loop shape. In an embodiment, the first elongate member 110 may be configured to couple the first dilator. In an embodiment the first elongate member 110 may couple the first dilator and then extend along a lumen of the first dilator and extend out of the lumen of the first dilator such that the first elongate member 110 can be configured to be removed by a mere pulling of an extended portion extending out of the lumen of the first dilator. In an embodiment, the first sleeve 104, or the first sleeve 104 and the implant 102 can include one or more holes that facilitate extension of the first elongate member 110 along the first sleeve 104 and the implant 102.

In an embodiment, a portion of the first elongate member 110 is configured to provide slack or a slack portion in the first elongate member 110 and the slack portion is accessible to an operator such that the operator can cut the slack portion to decouple the first sleeve 104 from the first portion of the implant 102.

In accordance with an embodiment, the second elongate member 112 can be configured to extend from the second dilator to the implant 102 and the second sleeve 106 such that the second elongate member 112 extends externally at some portion of the implant 102 and the second sleeve 106, and pierces through and extends within the second sleeve 106 and the implant 102 at some other portion. In accordance with these embodiments of threading, the second elongate member 112 may extend from the second dilator to and along the second sleeve 106 and the second portion of the implant 102 and then may traverse back toward the second dilator thereby forming a loop shape. In an embodiment, the second elongate member 112 may be configured to couple the second dilator. In an embodiment the second elongate member 112 may couple the second dilator and then extend along a lumen of the second dilator and extend out of the lumen of the second dilator such that the second elongate member 112 can be configured to be removed by a mere pulling of an extended portion extending out of the lumen of the second dilator. In an embodiment, the second sleeve 106, or the second sleeve 106 and the implant 102 can include one or more holes that facilitate extension of the second elongate member 112 along the second sleeve 106 and the implant 102.

In an embodiment, a portion of the second elongate member 112 is configured to provide a slack in the second elongate member 112 and the slack portion is accessible to an operator such that the operator can cut the slack portion to decouple the second sleeve 106 from the second portion of the implant 102.

In accordance with some embodiments, the first elongate member 110, the second elongate member 112, and the third elongate member 114 can be configured in a single piece of thread.

In some embodiments, the color of the first elongate member 110, the second elongate member 112, and the third elongate member 114 are different. In some embodiments, the color of the first elongate member 110 and the second elongate member 112 is same, which is distinct from the color of the third elongate member 114. This helps in easy distinction between the first and second elongate members 110 and 112, and the third elongate member 114, especially when the third elongate member 114 is cut for removal and disengagement of sleeves 110 and 112 as described below in conjunction with FIG. 8. In some other embodiments, the color of all the elongate members 110, 112, and 114 may however be kept the same, and the physician or the doctor may distinguish between the third elongate member 114 and the first and second elongate members 110 and 112 based on his perception of visual feedback or experience.

In accordance with the embodiments described above, the sleeves 104 and 106 are coupled to the implant 102 with two elongate members—the first elongate member 110 and the second elongate member 114. In some other embodiments, however, the implant 102 can be coupled to the sleeves 104 and 106 through a single elongate member that may be referred to as an elongate member for simplicity of description. In these embodiments, the elongate member is configured to removably couple the implant 102 with the first sleeve 104 and the second sleeve 106. The elongate member extends from the first portion 116 to the mid portion 120 of the implant 102 and past the mid portion 120 such that the elongate member exits the implant 102 through the mid portion 120 and forms a loop near the mid portion 120. The elongate member is further configured to enter the implant 102 through the mid portion 120 and extend from the mid portion 120 to the second portion 118 of the implant 102.

The elongate member extends from the first portion 116 of the implant 102 such that the elongate member is threaded in from the first surface of the implant 102 to the second surface of the implant 102 and then threaded out from the second surface to the first surface of the implant 102 and further threaded in from first surface to the second surface of the implant 102 and so on such that the elongate member forms a running stitch similar to the running stitch as described above. The single elongate member is used to couple the first sleeve 104 and the second sleeve 106 with the implant 102. In accordance with some embodiments, the single elongate member may extend from the first portion 116 to the mid portion 120 and then exit out from the implant 102 to extend and exit through the tab 108 and form a loop near and around the tab 108. The elongate member 110 then extends from the tab 108 to the second portion 118. In this manner, the single elongate member extends from the first portion 116 through the tab 108 and to the second portion 118 of implant 102. Further, in these embodiments, another elongate member similar to the third elongate member 114 as described above may be used to couple the implant 102 with the tab 108. However, in still some embodiments, the implant 102 may not be separately coupled to the tab 108 through the separate third elongate member 114.

The above described embodiments utilize the tab in the medical assembly. However, in some cases the medical assembly may not include any tab. In such cases, the first elongate member 110 and the second elongate member 112 (in case of multiple elongate members) or the elongate member (if there is only one elongate member) are configured to exit the mid portion 120 of the implant 102 and form a loop or a knot kind of structure around or close to the mid portion 120 without any requirement of the tab 108. The first elongate member 110 and the second elongate member 112 or the elongate member (if there is only one elongate member) can be removed just by pulling them at the loop.

In accordance with some embodiments, the single elongate member that couples the sleeves 104 and 106 with the implant 102, and the third elongate member can be configured in a single piece of thread.

In accordance with some embodiments, a carrier, dart, or an anchor or a combination thereof can be incorporated in the medical assembly 100.

In accordance with some embodiments, the medical assembly 100 can be used to treat incontinence.

FIG. 2A is a perspective view of a medical assembly 200 in accordance with an embodiment of the present invention.

The medical assembly 200 includes an implant 202, a first sleeve 204, a second sleeve 206, a tab 208, a first elongate member 210, a second elongate member 212 and a third elongate member 214.

The implant 202 has a first portion 216, a second portion 218 and a mid portion 220 between the first portion 216 and the second portion 218. In some embodiments, the mid portion 220 of the implant 202 is de-tanged (without tangs). The length of the de-tanged section can vary based on surgical requirements or location of placement inside the patient's body. In some embodiments, the first portion 216 and the second portion 218 may include tangs such that upon placement of the implant 202, the first portion 216 and the second portion 218 of the implant can interact with bodily tissues. The implant 202 can be formed from various materials such as polymeric material as described above in conjunction with FIG. 1.

The medical assembly 200 as illustrated in FIG. 2A further includes the first sleeve 204 and the second sleeve 206 configured to shield the first portion 216 and the second portion 218 of the implant 202. In some embodiments, the first sleeve 204 and the second sleeve 206 can be thin wall flat tubes. In some embodiments, the first sleeve 204 and the second sleeve 206 are made of polymer and may be colored blue for easy visualization. In other embodiments, the first sleeve 204 and the second sleeve 206 can be manufactured from an opaque or a transparent plastic film. The transparent plastic film enables visual examination of the implant 202. The first sleeve 204 and the second sleeve 206 be single or multiple ply. The first sleeve 204 and the second sleeve 206 can be made by extrusion or sandwiching two sheets of polymer together.

Each of the first sleeve 204 and the second sleeve 206 includes a proximal end portion 222 and 224 and a distal end portion 226 and 228 with a length 230 and 232 extending between the proximal end portion 222 and 224 and the distal end portion 226 and 228 such that the length 230 of the first sleeve 204 is sufficient to envelop or shield the first portion 216 of the implant 202 and length 232 of the second sleeve 206 is sufficient to shield the second portion 218 of the implant 202. In various embodiments, the first portion 216 is a first end portion of the implant 202 and the second portion 218 is the second end portion of the implant 202 such that the first sleeve 204 and the second sleeve 206 are configured to enclose the first end portion and the second end portion respectively of the implant 202. The first sleeve 204 and the second sleeve 106 are together hereafter referred to as sleeves 204 and 206 for simplicity of the description.

In some embodiments, the sleeves 204 and 206 can have a variety of shapes. For example, the sleeves 204 and 206 can be rectangular with a tapered proximal end portion and the distal end portion 226 and 228 such that the sleeves 204 and 206 can be easily withdrawn without catching a tissue. In some embodiments, the sleeves 204 and 206 are shaped in the form of hollow tubes or envelopes such that a hollow space within the sleeves 204 and 206 define lumen 240 and 242 therein. The lumen 240 and 242 of the sleeves 204 and 206 is configured to receive first portion 216 and the second portion 218 which are the first end portion and the second end portion of the implant 202. The first end portion and the second end portion may be respectively disposed within the lumen 240 and 242 of the first sleeve 204 and the second sleeve 206. In some embodiments, the implant 202 may be free-floating within the first sleeve 204 and the second sleeve 206. Alternatively, the implant 202 may be fixed to the sleeves 204 and 206.

In some embodiments, the lumen 240 and 242 of the sleeves 204 and 206 have width 246 and 248 which is larger than width of the implant 202 at the first and the second end portion that are configured to be covered by the sleeves 204 and 206. This allows housing of the end portions 216 and 218 of the implant 202 within the lumen 240 and 242 of the sleeves 204 and 206. In some other embodiments, the proximal end portions 222 and 224 of the sleeves 204 and 206 are slightly tapered to allow easy withdrawal without catching tissues. In some embodiments, the sleeves 204 and 206 can be made of resilient or flexible material such that the width of the lumen 240 and 242 is smaller than the width of the implant 202 in a normal condition. However, since the sleeve 204 and 206 is configured to be stretched due to its flexible material, the width of the lumen 240 and 242 can be increased to an extent that makes the receipt of the implant 202 possible within the lumen 240 and 242.

In certain embodiments of the present invention, the first and the second sleeves 204 and 206 shield only the first portion 216 and the second portion 218 the implant 202 such that the mid portion 220 of the implant 202 remains un-shielded. The un-shielded mid portion 220 is configured to interact to a bodily tissue upon placement. In certain other embodiments, the first sleeve 204 and the second sleeve 206 together encloses a maximum of half of a total length of the implant 202, thus shielding half of the implant 202 and leaving the other half of the implant 202 un-shielded. In some embodiments, the first sleeve 204 and the second sleeve 206 together encloses less than half of the total length of the implant 202. In some other embodiments, the first sleeve 204 and the second sleeve 206 together encloses half of the total length of the implant 202. In some other embodiments, the first sleeve 204 and the second sleeve 206 together encloses about half of the total length of the implant 202. In some other embodiments, the first sleeve 204 and the second sleeve 206 may together enclose slightly or substantially more than half of the total length of the implant 202. In some embodiments, the length of the implant 202 that is shielded with the sleeves 204 and 206 can vary based on requirements.

Figure 2B:
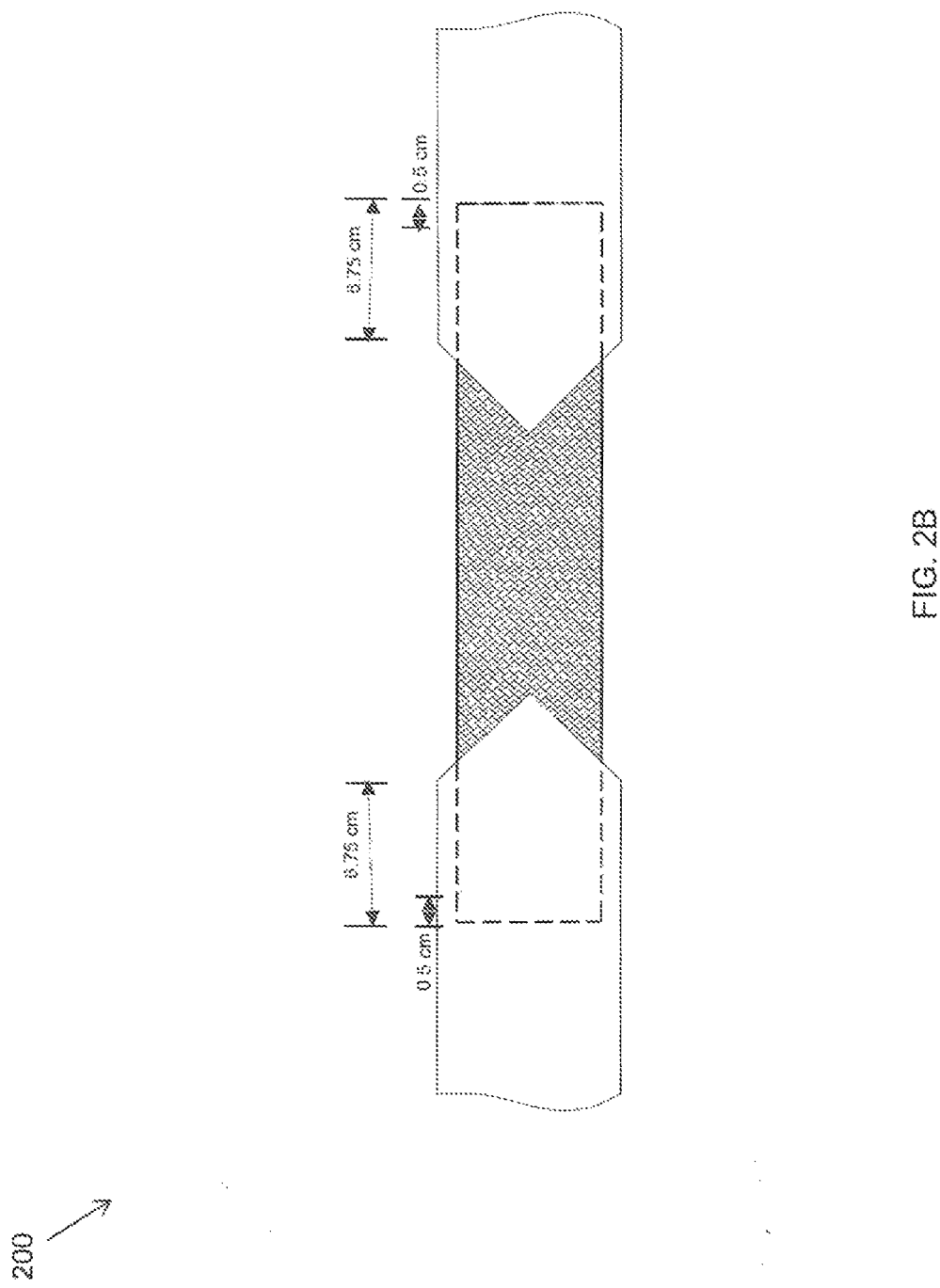
Figure 2C:
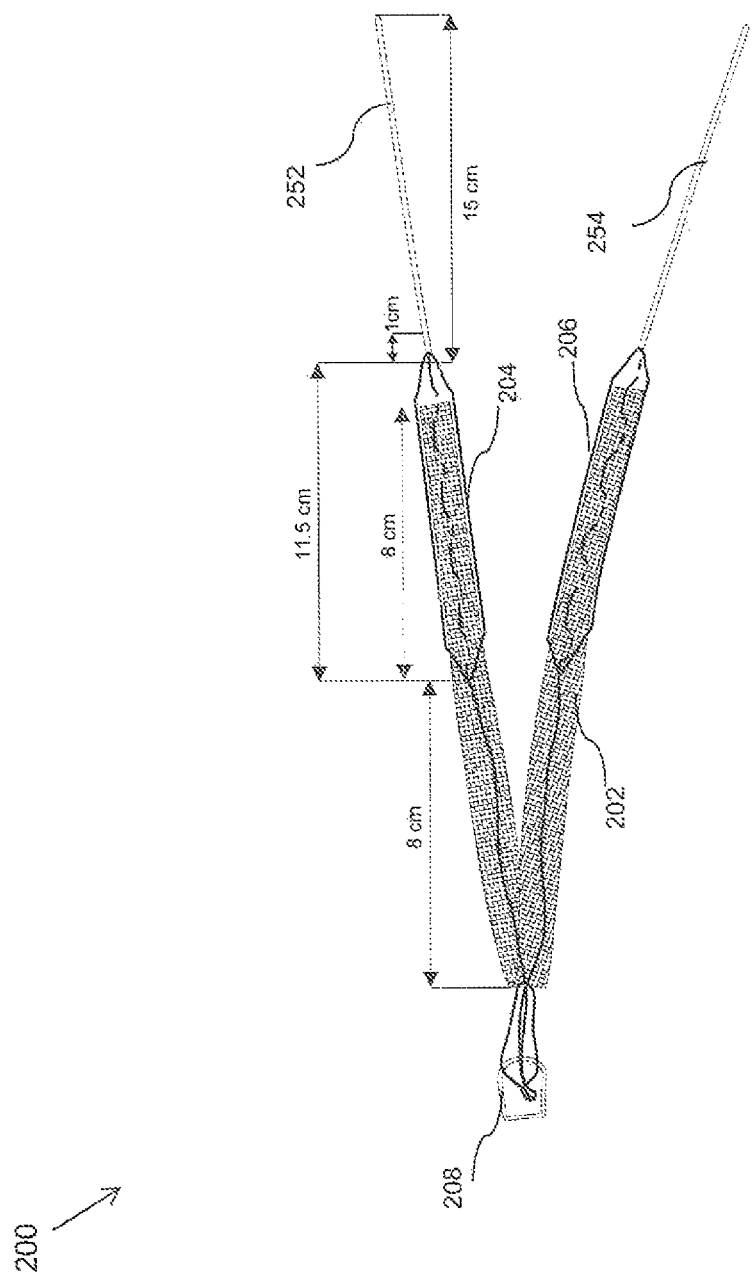

In some embodiments, for example, as shown in FIG. 2B, the implant 202 has an initial length of 28 cm and portions of the implant 202 at its ends are folded over to create a working length of 27 cm. In some embodiments, the folds can be secured to the implant 202 by a suture, tack, or the like fasteners. The working length can be created by folding a length of 0.5 cm on each side of the implant 202. The folded length can be 0.5 cm, 1 cm, 2 cm or any preferred length to increase the holding strength of the sling via tangs, in accordance with various other embodiments. In some embodiments, the fold is secured to the implant 202 by a suture, tack or the like elements or fasteners. A working length of about 27 cm would maintain the entire length of the sling within a patient and require no trimming after placement, in accordance with some embodiments. For a 27 cm working length of the implant 202, 25% maximum of the implant 202 is covered with the sleeves 204 and 206 or 6.75 cm maximum of each of the implant 202 ends are covered, in accordance with some embodiments of the present invention. In accordance with some embodiments, exemplary dimensions of some portions or components of the medical assembly 200 are shown in FIG. 2C. It must be appreciated that various other dimensions of these portions and components of the medical assembly 200 can be possible.

Figure 5:
FIG. 5 is perspective view of an association skive, in accordance with an embodiment of the present invention.
Figure 5:

Referring again to FIG. 2A, in certain embodiments of the present invention, the medical assembly 200 may also include a first dilator 252 configured to be coupled to the first sleeve 204, and a second dilator 254 configured to be coupled to the second sleeve 206. The first dilator 252 and the second dilator 254 are configured to be coupled respectively to the distal end 226 and 228 of the first sleeve 204 and the second sleeve 206. The first dilator 252 and the second dilator 254 are heat bonded respectively to the first sleeve 204 and the second sleeve 206. In some embodiments, the first dilator 252 and the second dilator 254 are further configured to be coupled to a delivery device 262, as shown in FIG. 2D. The delivery device 262 is a medical instrument that can be used to facilitate delivery of the medical assembly 200 including the implant 202 within the patient's body. A few examples of the delivery devices may include the Boston Scientific Corporation Obtryx™, Lynx™, Advantage™, Prefyx™ delivery device or any other delivery device. In some embodiments, the dilator is small in diameter to provide a less invasive surgery. The dilator can be further associated with an association skive. An exemplary association skive is shown in FIG. 5 later.

As mentioned above, the medical assembly 200 further includes the tab 208 configured to be coupled to the implant 202. The tab 208 is configured to identify the mid portion 220 of the implant 202 and provide for equal length of the implant 202 on each side of a body tissue or organ required to be balanced such as a urethra of the patient. In some embodiments, the tab 208 can be colored for easy visualization during a surgical procedure.

The tab 208 is further provided with a slot 256 to receive the first elongate member 210, the second elongate member 212 and the third elongate member 214. In certain embodiments, the first elongate member 210 is configured to removably couple the implant 202 with the first sleeve 204 such that the first elongate member 210 extends from the first portion 216 to the mid portion 220 of the implant 202 and past the mid portion 220 and exits the implant 202 through the mid portion 220. The second elongate member 212 is configured to removably couple the implant 202 with the second sleeve 206 such that the second elongate member 212 extends from the second portion 218 to the mid portion 220 of the implant 202 and past the mid portion 220 and exits the implant 202 through the mid portion 220. The first elongate member 210 and the second elongate member 212 are coupled together at the tab 208 or in close proximity of the tab 208.

In some other embodiments, the tab 208 may include only a single slot 256 to receive all of the three elongate members—the first elongate member 210, the second elongate member 212, and the third elongate member 214.

Figure 2E:
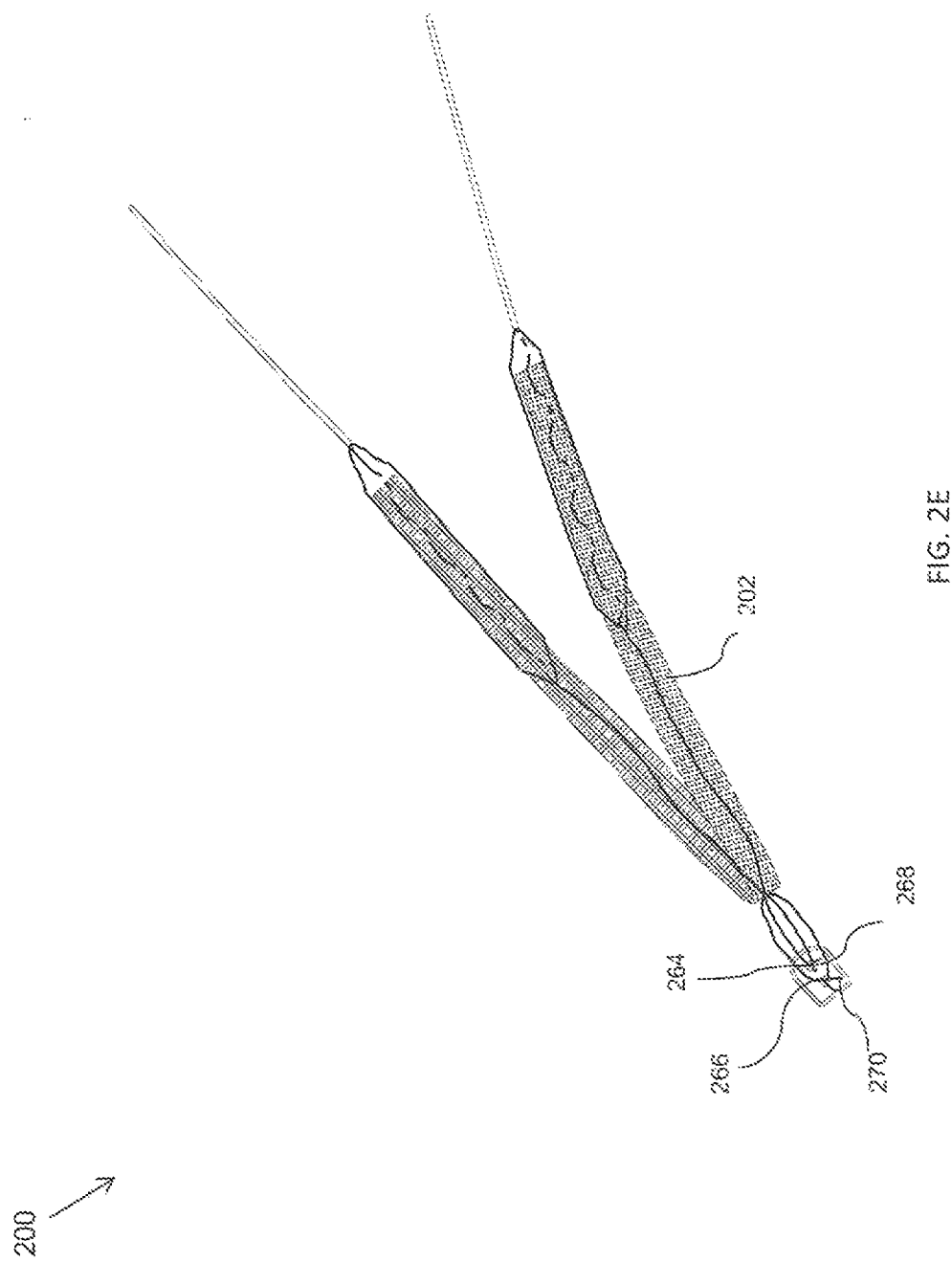

In some embodiments, the tab 208 may include multiple slots to receive the first elongate member 210, the second elongate member 212, and the third elongate member 214 as shown in FIG. 2E. As illustrated in FIG. 2E, the medical assembly 200 includes two slots to receive the first elongate member 210, the second elongate member 212, and the third elongate member 214. A first slot 264 is configured to receive the first elongate member 210 and the second elongate member 212 whereas the second slot 266 is configured to receive the third elongate member 214. The first elongate member 210 and the second elongate member 212 are coupled together at the tab 208 to form a first knot 268 at the tab 208 or in close proximity of the tab 208. The first knot 268 not only couples the tab 208 to the first elongate member 210 and the second elongate member 212, but also the first elongate member 210 and the second elongate member 212 to each other at the tab. The first knot 268 can be considered as a junction where the first elongate member 210, the second elongate member 212 and the tab 208 are contacted or coupled. The third elongate member 214 forms a second knot 270 at the tab 208.

The tab 208 may be made of any material known in the art, such as, for example, polyethylene, PTFE, or EPTFE, and may be of any color, such as blue, to assist the user in viewing the tab 208. The tab 208 may be sized and otherwise configured to assist in positioning a portion of the implant 202 and/or the sleeves 204 and 206 within the body of a patient.

Figure 2F:
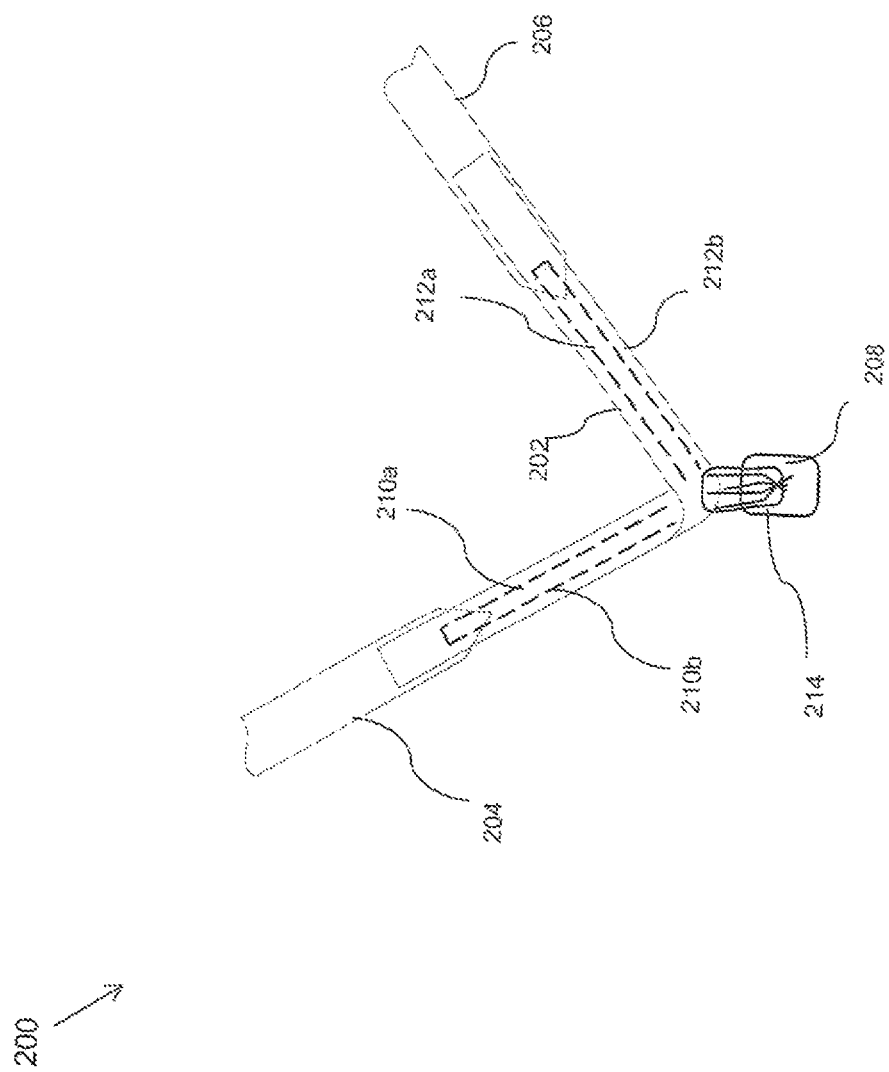

The first elongate member 210 and the second elongate member 212 include one of a thread, a medical suture, a filament, a rope, and the like. In some embodiments, as shown in FIG. 2A, the first elongate member 210 and the second elongate member 212 have a single suture or thread running along a portion of length of the implant 202. However, in some other embodiments, the first elongate member 210 and the second elongate member 212 may have multiple sutures or threads running along a portion of length of the implant 202 as shown in FIG. 2F. For example, the first elongate member 210 may have multiple sutures or threads such as 210a and 210b that may be provided for coupling the implant 202 with the sleeves 204 and 206 such that the sutures or threads are placed adjacent to one another for increasing strength of the coupling. In some embodiments, the first elongate member 210 including the sutures or threads 210a and 210b extends from the first portion 216 to the mid portion 220 of the implant 202 such that the sutures or threads 210a and 210b exit the implant 202 at mid portion 220. Similarly, the second elongate member 212 including the sutures or threads 212a and 212b extends from the second portion 218 to the mid portion 220 of the implant 202 such that the sutures or threads 212a and 212b exit the implant 202 at mid portion 220. After exiting the implant 202, the free ends of the sutures or threads 210a and 210b, 212a, and 212b are tied together to form a knot that is configured to be coupled with the tab 208. In some other embodiments, the third elongate member 214 passes through the mid portion 220 of the implant 202 and couples with the tab 208 such that cutting the third elongate member 214 leaves the tab 208 still coupled with the implant 202. The tab 208 is coupled with the implant 202 through the first elongate members 210 and the second elongate member 212.

Referring again to FIG. 2A, in some embodiments, the first elongate member 210 and the second elongate member 212 couple the implant 202 with the first sleeve 204 and the second sleeve 206 respectively in a manner that the first elongate member 210 and the second elongate member 212 are threaded in and out through the implant 202. Each of the first elongate member 210 and the second elongate member 212 first passes from the first surface 276 of the implant 202 to the second surface 278 and then from second surface to the first surface 276, thereby forming one stitch. Similarly, this pattern of stitches continues to a certain length of the implant 202 to form multiple stitches in a sequence that may be termed as a running stitch. The running stitch thus refers to a series of stitches that hold the sleeves 204 and 206 and the implant 202 through frictional resistance together. This has been described in conjunction with FIG. 1. The elongate members 212 are threaded in and out of the implant 202 and sleeves 204 and 206 in a manner that the frictional resistance is reached to an extent where the elongate members can keep the sleeves 204 and 206 and the implant 202 coupled together but may allow decoupling of the implant 202 and the sleeves 204 and 206 when the elongate members are pulled by overcoming the frictional resistance. In certain embodiments, the first elongate member 210 and the second elongate member 212 may have no free ends such that one end is tied to the tab 208 and the other end is tucked into the sleeves 204 and 206. In some embodiments, the first elongate member 210 and the second elongate member 212 may have one free end such that one end is tied to the tab 208 and the other end is free. The free end may further extend from end portions of the implant 202 beyond the dilators 252 and 254 to form association loops 272 and 274 as illustrated in FIG. 2G. The association loops 272 and 274 are configured to provide an association with the delivery device. In some embodiments, the association loop can associate the delivery device with an L shape slot or a reverse L shape slot.

As mentioned above, the medical assembly 200 includes the third elongate member 214 configured to pass through the mid portion 220 of the implant 202 and form a loop 260 such that the loop 260 couples the mid portion 220 of the implant 202 with the tab 208. In some embodiments, the third elongate member 214 is a thread or a suture and the like that is a part separate from the implant 202 to be removably coupled to the implant 202 and the tab 208 for coupling the tab 208 with the implant 202 through the loop 260. In other embodiments, the third elongate member 214 can be an integral part of the implant 202 such that the third elongate member 214 is weaved into the implant 202 center and extend from there outside the implant 202 to form the loop 260 that is configured to receive the tab 208 for coupling the tab 208 with the implant 202. The third elongate member 214 is threaded in and out through the mid portion 220 of the implant 202 such that the third elongate member 214 passes through the implant 202 at the mid portion 220 and then form a loop type of structure 260. In some embodiments, free ends of the third elongate member 214 can be tied together to form a knot referred to as a second knot 270 as shown in FIG. 2E. In accordance with these embodiments, the third elongate member 214 first passes through the implant mid portion 220 and then through a slot 256 in the tab 208 and then knotted together to couple the tab 208 with the implant 202. This pattern of association of the implant 202 with the tab 208 is configured to disassociate the implant 202 from the tab 208 by cutting the third elongate member 214 or removing the second knot 270.

In accordance with the embodiments described above, the tab 208 is therefore coupled to the third elongate member 214 directly through the second knot 270 and also to the first elongate member 210 and the second elongate member 212 through the first knot 268 as shown in FIG. 2E formed at the tab 208. The first knot 268 not only couples the tab 208 respectively to the first elongate member 210 and the second elongate member 212 but also the first elongate member 210 and the second elongate member 212 to each other at the tab. Therefore, the first knot 268 holds the first and the second elongate members 210 and 212 also together. Therefore, the first elongate member 210 and the second elongate member 212 are together configured to be removed when the tab 208 is pulled after cutting the second knot 270 formed at the tab 208 by the third elongate member 214. In some embodiments, the first elongate member 210 and the second elongate member 212 can be removed by cutting the third elongate member 214 at a location other than the second knot 270.

In some embodiments, the color of the first elongate member 210, the second elongate member 212, and the third elongate member 214 is different. In some embodiments, the color of the first elongate member 210 and the second elongate member 212 is same which is distinct from the color of the third elongate member 214 this helps in easy distinction between the first and second elongate members 210 and 212, and the third elongate member 214 especially when the third elongate member 214 is cut for sleeves 204 and 206 removal and disengagement, as described below in conjunction with FIG. 7. In some other embodiments, the color of all the elongate members 210, 212, and 214 may however be kept same, and the physician or the doctor may distinguish between the third elongate member 214 and the first and second elongate members 210 and 212 based on his perception of visual feedback or experience. FIG. 2H illustrates an enlarged view of the medical assembly 200 shown in FIG. 2A. FIG. 2I is a cross-sectional side view of the medical assembly 200 illustrated in FIG. 2A.

FIG. 2J illustrates the medical assembly 200 without the tab 208. As illustrated in FIG. 2J, the medical assembly 200 includes the implant 202 having the first portion 216, the second portion 218 and the mid portion 220. The medical assembly 200 further includes the first sleeve 204 and the second sleeve 206. The first sleeve 204 and the second sleeve 206 are configured to be removably coupled to the implant 202 with a single elongate member 280. In accordance with some embodiments, the sleeves 204 and 206 are coupled to the implant 202 using a single elongate member 280 only that can be referred to as the elongate member 280, as shown in FIG. 2J.

The single elongate member 280 extends from the first portion 216 to the mid portion 220 of the implant 202 and past the mid portion 220 such that the elongate member 280 exits the implant 202 through the mid portion 220 and forms a loop 282 near the mid portion 220. The elongate member 280 further configured to enter the implant 202 through the mid portion 220 and extends from the mid portion 220 to the second portion 218 of the implant 202.

The elongate member 280 extends from first portion 216 of the implant 202 such that the elongate member is threaded in from the first surface 276 of the implant 202 to the second surface 280 of the implant 202 and then threaded out from the second surface 278 to the first surface 276 of the implant 202 and further threaded in from first surface 276 to the second surface 278 of the implant 202 and so on such that the elongate member 280 forms a running stitch across a portion of the implant 202. The single elongate member 280 couples the first sleeve 204 with the implant 202 and extends from first portion 216 to the mid portion 220 of the implant 202. At the mid portion 220 of the implant 202 the single elongate member 280 exits the implant 202 and forms a loop 282 near the mid portion 220. After forming the loop 282 the elongate member enters the implant 202 at the mid portion 220 and extends from the mid portion 220 to the second portion 218 of the implant 202 thereby coupling the second sleeve 206. Further, as shown in FIG. 2J, both the ends of the single elongate member 280 may be free such that pulling either of the ends of the single elongate member 280 decouples the first sleeve 204 and the second sleeve 206 from the implant 202. In some embodiments, the first sleeve 204 and the second sleeve 206 are configured to be decoupled by pulling the loop 282 formed near the mid portion of the implant 202.

Figure 3A:
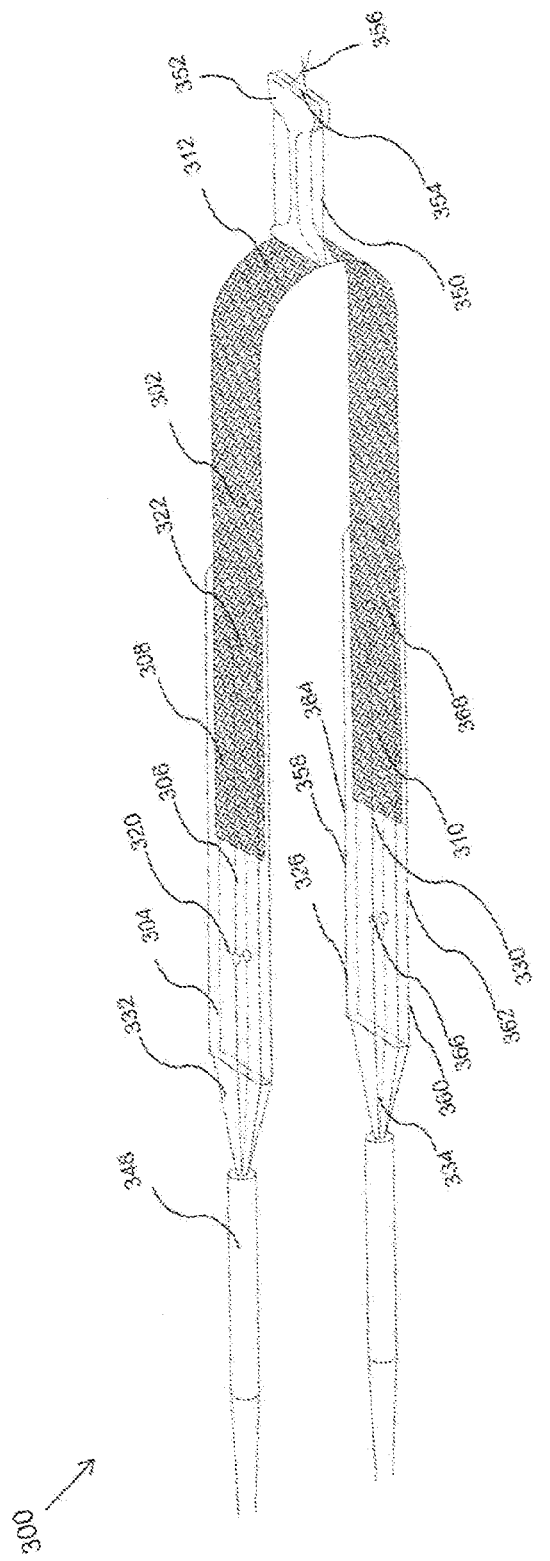
FIG. 3A is a perspective view of a medical assembly, in accordance with an embodiment of the present invention.

FIG. 3A is a perspective view of a medical assembly 300. In some embodiments, the medical assembly 300 includes an implant 302, a sleeve 304, and an elongate member 306. The implant 302 has a first portion 308, a second portion 310 and a mid portion 312 between the first portion 308 and the second portion 310. The implant 302 can be similar to the implants described above in conjunction with various figures.

In some embodiments, the sleeve 304 as shown in FIG. 3A includes a top layer 314, a bottom layer 316, and a lumen 318 defined between the top layer 314 and the bottom layer 316. In some embodiments, a first hole 320 is provided on the top layer 314 and a second hole 322 is provided on the bottom layer 316. The first hole 320 and the second hole 322 are respectively defined along a thickness 324 of the top layer 314 and the bottom layer 316.

In some embodiments, the sleeve 304 is a first sleeve 304 configured to be coupled to the first portion 308 of the implant 302. In some other embodiments, the medical assembly 300 includes a second sleeve 326 similar to the first sleeve 304 such that the second sleeve 326 is configured to be coupled to the second portion 310 of the implant 302. In some embodiments, both the first sleeve 304 and the second sleeve 326 cover around 60% of a length 328 of the implant 302. Then second sleeve 326 may also include a first hole 366 and a second hole 368 similar to the holes 320 and 322 in the first sleeve 304.

In some embodiments, the elongate member 306 is configured to pass through the first hole 320, along the lumen 318 and the second hole 322 and couples the implant 302 with the sleeve 304. In some embodiments, the elongate member 306 is a first elongate member 306 configured to removably couple the first portion 308 of the implant 302 with the first sleeve 304. In some embodiments, the medical assembly 300 also includes a second elongate member 330 similar to the first elongate member 306 that is configured to pass through holes in the second sleeve 326.

As illustrated in FIG. 3A, the first elongate member 306 extends from a distal end portion 332 of the first sleeve 304 to the first portion 308 of the implant 302 thereby coupling the first portion 308 of the implant 302 with the first sleeve 304. The first elongate member 306 extends in and out across the first sleeve 304 through the first hole 320 on the top layer 314 along the lumen 318 of the first sleeve 304, and further through the second hole 322 on the bottom layer 316 of the first sleeve 304.

In some embodiments, the implant 302 can be a mesh based device such that the first elongate member 306 passes through a mesh cell of the implant 302. In some embodiments, the implant 302 can be a non-mesh based device such that the non-mesh based device includes a hole (not shown) that is configured to facilitate passing of the first elongate member 306 through the implant 302.

In some embodiments, the second elongate member 330 extends from the distal end portion 334 of the second sleeve 326 to the second portion 310 of the implant 302 and extends across the first hole 366 of the top layer 358 and the second hole 368 of the bottom layer 360 of the second sleeve 326 thereby coupling the second portion 310 of the implant 302 with the second sleeve 326 in a manner similar to the first elongate member 306. In accordance with some embodiments, the first sleeve 304 and the second sleeve 326 may include at least one hole similar to the holes 320 and 322. In case of multiple holes, the first elongate member 306 and the second elongate member 330 should pass through at least one hole in the respective sleeves 304 and 326.

In some embodiments, the first elongate member 306 can be oriented linearly and centered along the length 362 of the first sleeve 304. Similarly, the second elongate member 326 can be oriented linearly and centered along the length 364 of the second sleeve 326.

In some embodiments, the first elongate member 306 as shown in FIG. 3B, originates from the distal end portion 332 of the first sleeve 304 and extends to the first hole 320 formed at the top layer 314 of the first sleeve 304 in a manner that the first elongate member 306 includes a portion 336 laid at a surface external to the top layer 314. The portion 336 is configured to provide a slack in the first elongate member 306 and is accessible to an operator such that the operator can cut the exposed portion to decouple the first sleeve 304 from the first portion 308 of the implant 302. In such embodiments, at least one portion 336 of the first elongate member 306 is configured to lay external to the top layer 314 or the bottom layer 316 of the first sleeve 304. The portion 336 can be referred to as first portion 336 of the first elongate member 306.

As shown in FIG. 3B, the first elongate member 306 is shown to pass through multiple holes similar to the holes 320 and 322. In some embodiments, hole 340 may be made in line with hole 322 and holes 338 and 344 may be made in line through top layer 314 and bottom layer 316. In some embodiments, not all holes are used. In accordance with the illustrated embodiment of FIG. 3B, the first elongate member 306 passes through the first hole 320 at the top layer 314 of the first sleeve 304, and then extends across a portion within the lumen 318 of the first sleeve 304. The first elongate member 306 extends from the lumen 318 of the first sleeve 304 to a third hole 338 at the top layer 314 of the first sleeve 304. The first elongate member 306 then extends from the third hole 338 to a fourth hole 340 at the top layer 314 of the first sleeve 304. A second portion 342 of the first elongate member 306 that lies between the third hole 338 and the fourth hole 340 is external to the top layer 314 and is accessible to the operator. The second exposed portion 342 of the first elongate member 306 is configured to provide a slack. The slack provided by the first portion 336 and the second portion 342 enables an operator to pull or cut the first elongate member 306 to decouple the first sleeve 304 from the implant 302 without cutting the first sleeve 304. The first elongate member 306 then passes from the fourth hole 340 at the top layer 314 of the first sleeve 304 to the first portion 308 of the implant 302 and further through the second hole 322 at the bottom layer 316 of the first sleeve 304. The first elongate member 306 then extends from the second hole 322 to a fifth hole 344 of the bottom layer 316 of the first sleeve 304. A third portion 346 of the first elongate member 306 between the second hole 322 and the fifth hole 344 of the bottom layer 316 of the first sleeve 304 is exposed and is accessible to the operator (for example, if the medical device extends through the skin incision). The first elongate member 306 then moves from the fifth hole 344 into the lumen 318 of the first sleeve 304 and extends to the distal end portion 332 of the first sleeve 304. In this manner, the first elongate member 306 couples the first sleeve 304 and the first portion 308 of the implant 302 together. Both free ends of the first elongate member 306 lying at the distal end portion 332 of the first sleeve 304 can be further coupled with a first dilator 348. The free ends of the first elongate member 306 can be coupled to the first dilator 348 through various coupling elements or modes. The various coupling elements or modes may include gluing, stapling, knotting or ultrasonic welding. In some embodiments, an excess slack at the first portion 336, the second portion 342, the third portion 346 or along a rest of the portion of the first elongate member 306 can be removed or adjusted such that the length of the first elongate member 306 is configured to prevent migration or dislodgement or movement of the medical assembly 300 or a portion of the medical assembly 300 during delivery of the implant 302.

In some embodiments, the excess slack, for example, at the first portion 336 of the first elongate member 306 is cut to release the implant 302 from the first sleeve 304 thereby resulting in two free ends of the first elongate member 306. The first dilator 348, external to the body, is pulled in the direction of arrow A, as shown in FIG. 3B or away from the body. In an embodiment, the arrow A can represent a direction along the vaginal opening or vaginal passageway. In another embodiment, the arrow A can specify a direction different from a direction of the vaginal opening. In such examples, the direction of A can be any other bodily opening or a passageway created through incisions along a body portion such as skin incisions, groin incisions, midline incisions, incisions in thigh, buttock or any other bodily location. The dilator 348 is pulled out through the passageway thus created. In some embodiments, the dilator 348 can be pulled away from the reminder of the medical assembly 300 while the dilator 348 is coupled to the first sleeve 304 and the first elongate member 306. Thus, the dilator 348, the first elongate member 306, and the first sleeve 304 may be pulled away from the implant 302 together at one time. In other embodiments, the dilator 348 can be pulled out from while the one end of the first elongate member 306 is still attached to the medical assembly 300 and the first elongate member 306 and the first sleeve 304 may be removed separately from the dilator 348. The cut free end of the first elongate member 306 unthreads from the first sleeve 304 and the implant 302 in a path of arrow B, as shown in FIG. 3B. The path of arrow B is the path travelled by the first elongate member 306 while unthreading and decoupling the first sleeve 304 from the implant 302, and removing the first elongate member 306 or the first dilator 348 from the body. The first elongate member 306 travels from the top layer 314 to the bottom layer 316 as the first dilator 348 is pulled in the direction of arrow A. The first sleeve 306 along with the first elongate member 306 is removed as a single part through the passageway that can be the vaginal opening or the skin incision. In some embodiments, the center tab (not shown) can be removed through the midline incision. In some embodiments, the first sleeve and the first elongate member can together be removed from the skin incisions.

It must be appreciated that threading of the first elongate member 306 with the implant 302 and the first sleeve 304 as discussed above is exemplary and various other ways may also be possible. Similarly, the second elongate member 330 can be threaded to couple the implant 302 with the second sleeve 326.

Figure 3C:
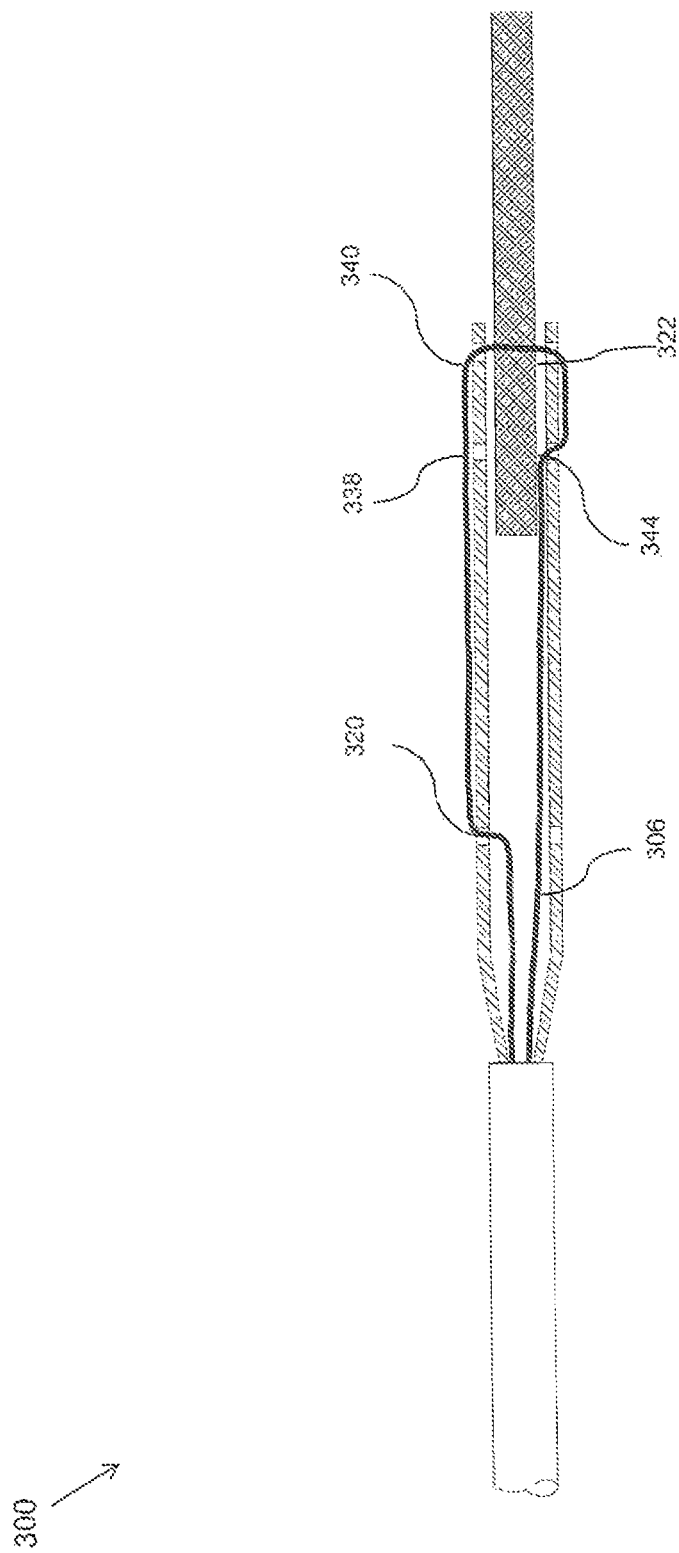

The first elongate member 306 and the second elongate member 330 can be threaded in various ways through the holes of the top layer 314 and the bottom layer 316 of the first sleeve 304 and the second sleeve 326. One such variation is illustrated in FIG. 3C, where the first elongate member 306 originates from the distal end portion 332 and extends from the lumen 318 of the first sleeve 304 to the first hole 320 of the top layer 314. The first elongate member 306 then extends out from the lumen 318 of the first sleeve 304 through the first hole 320 and lay exposed external to the top layer 314. The first elongate member 306 then extends from the first hole 320 directly to the fourth hole 340 and goes inside the lumen 318 again through the fourth hole 340. The first elongate member 306 then passes through the first portion 308 of the implant 302 and further moves out of the lumen 318 of the first sleeve 304 through the second hole 322 of the bottom layer 316. Further, the first elongate member 306 extends from the second hole 322 to the fifth hole 344 and from the fifth hole 344 to the lumen 318 of the first sleeve 304. The free ends of the first elongate member 306 is then knotted with and coupled to the first dilator 348. In another embodiment, as illustrated in FIG. 3D, the device 300D includes an elongate member 306D. The elongate member 306D extends from the dilator, through a portion of the implant, through an opening or hole 340D in the sleeve, and back to the dilator external to the sleeve. The end portions of the sleeve are coupled to the dilator and thus, the elongate member forms a loop to couple the dilator to the implant and the sleeve.

In some embodiments of the present invention, a third elongate member 350 as shown in FIG. 3A, is configured to pass through the mid portion 312 of the implant 302 and form a loop such that the loop is configured to couple the mid portion 312 of the implant 302 with a tab 352. In some embodiments, the third elongate member 350 first passes across a slot 354 of the tab 352 and then through the mid portion 312 of the implant 302. The third elongate member 350 further exits the implant 302 at the mid portion 312 and passes again through the slot 354 of the tab 352. Thus, both free ends of the third elongate member 350 lie near the tab 352. In some embodiments, the free ends can then form a knot 356 to couple the mid portion 312 of the implant 302 with the tab 352. In some embodiments, the third elongate member 350 presses or forces a portion of the tab 352 against the mid portion 312 of the implant 302.

Referring again to FIGS. 3A-3C, the first sleeve 304 and the implant 302 can be decoupled by pulling or cutting any of the first portion 336, the second portion 342 or the third portion 346 of the first elongate member 306. The first dilator 348 or the first sleeve 304 can then be pulled in order to remove the first sleeve 304 from the implant 302. The third elongate member 350 can be cut and the tab pulled by the operator to decouple the tab 352 and elongate member from the implant 302.

Figure 3E:
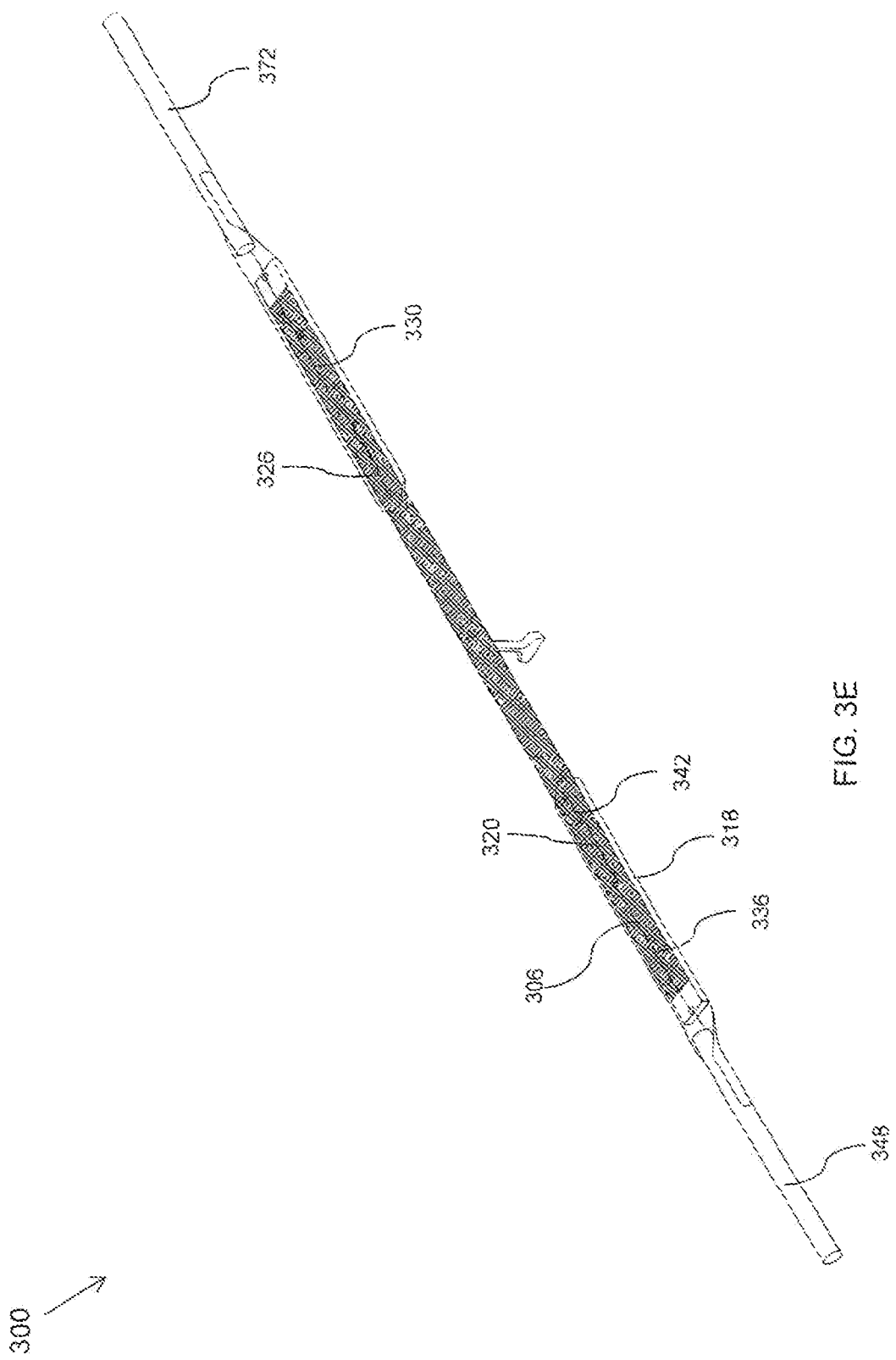
FIGS. 3E and 3F are perspective views of a medical assembly in accordance with some embodiments of the present invention.

As shown in FIG. 3E the first elongate member 306 is configured to couple the first sleeve 304 and the first portion 336 of the implant 302 such that the first portion 336 of the first elongate member 306 extends along the sleeve and lay external to the sleeve while the second portion 342 of the first elongate member 306 extends through the lumen 318 of the first sleeve 304 and across the implant 302, the first elongate member 306 extending between the first dilator 348 and the first sleeve 304 to form a loop structure of threading. In such embodiments, the first elongate member 306 can be configured to extend from the first dilator 348 to the implant 302 and the first sleeve 304 such that the first elongate member 306 extends externally at some portion of the implant 302 and the first sleeve 304, and pierces through and extends within the first sleeve 304 and the implant 302 at some other portion. In accordance with these embodiments of threading, the first elongate member 306 may extend from the first dilator to and along the first sleeve 304 and the first portion 336 of the implant 302, and then may traverse back toward the first dilator 348 thereby forming a loop shape.

In an embodiment, the first elongate member 306 may be configured to couple the first dilator 348. In an embodiment, the first elongate member 306 may couple the first dilator 348 and then extend along a lumen of the first dilator 348 and extend out of the lumen to form an association loop 374 (described in more detail below). In other embodiments, the association loop 374 may be separate from the first elongate member 306. In such embodiments, the first elongate member 306 is coupled to the first dilator 348 and the association loop 374 (which may be formed of an elongate portion of various types of materials, such as suture material or a metal material) is coupled to the first dilator 348. In some embodiments, the portion 336 of the first elongate member 306 that lay external to the first sleeve 304 and configured to provide a slack is accessible to an operator such that the operator can first cut the exposed portion to decouple the first sleeve 304 from the first portion 308 of the implant 302. In such embodiments, after cutting such as the portion 336, the first elongate member 306 and the first sleeve 304 are together configured to be pulled out of the body through skin incisions upon implantation of the implant 302 under urethra without cutting the first sleeve 304.

In some embodiments, the first sleeve 304, or the first sleeve 304 and the implant 302 can include one or more holes that facilitate extension of the first elongate member 306 along the first sleeve 304 and the implant 302. In some embodiments, the first sleeve 304 wraps around completely and attaches to the first dilator 348. In some other embodiments, the first sleeve 304 wraps around partially and attaches to the first dilator 348.

Figure 3F:
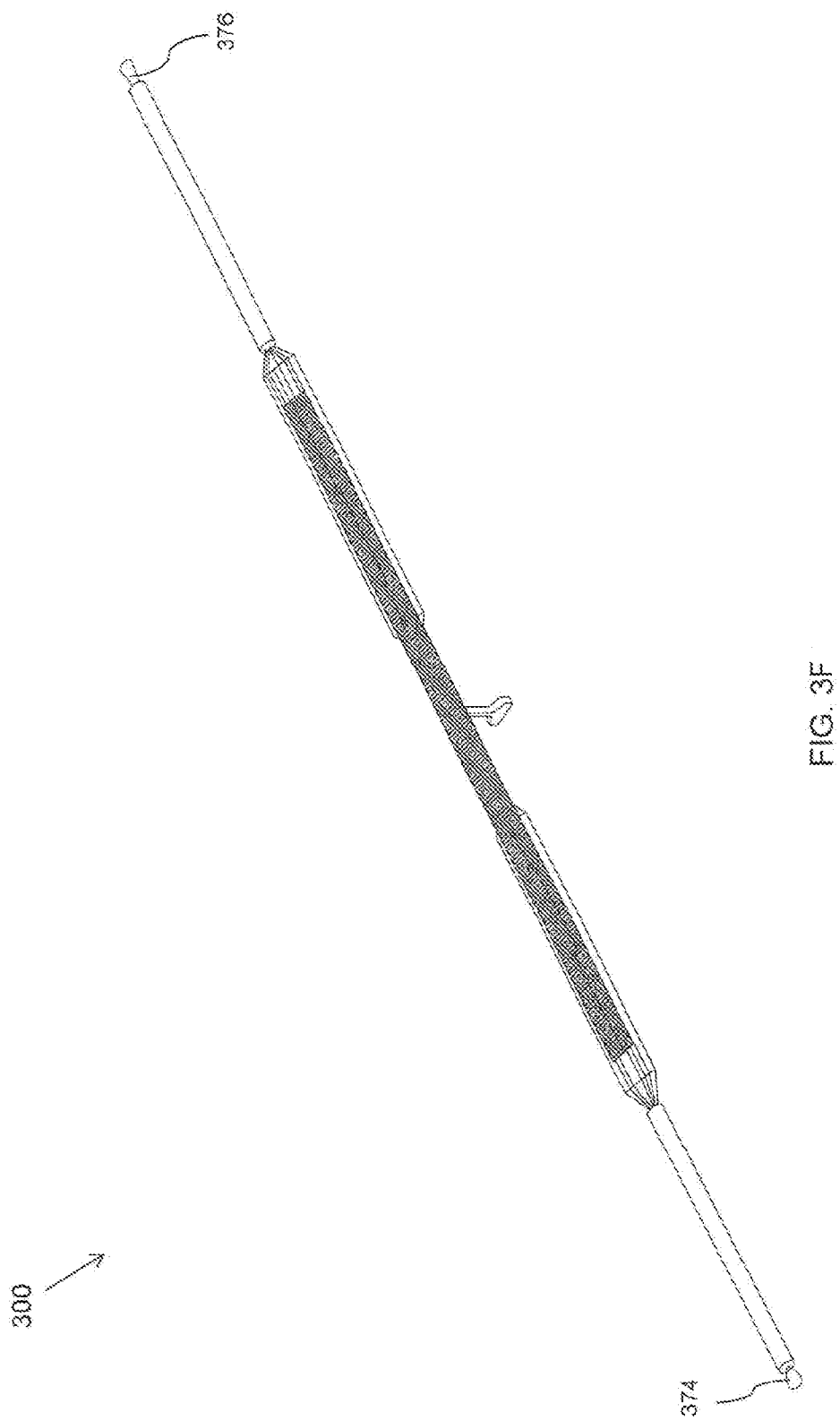

In some embodiments, an association loop can be formed, such as with a thread for an association of the dilators with a delivery device as shown in FIG. 3F. The association loop is provided at distal ends of the first dilator 348 and the second dilator 372 to associate the first dilator 348 and the second dilator 372 to the delivery device. The association loops 374 and 376 are configured to provide an association with the delivery device. In some embodiments, the association loops 372 and 374 can associate the delivery device with an L shape slot or a reverse L shape slot such as a BSC Obtryx Halo, Obtryx Curve or Lynx, after the delivery needle device has been passed through tissue.

Referring again to FIG. 3E, the medical assembly 300 includes the second dilator 372 and the second elongate member 330 similar to the first elongate member 306 and the first dilator 348. The second elongate member 330 extends from the second dilator 372, across a portion of the second sleeve 326, along a lumen 376 of the second sleeve 326, across a portion of the implant 302 and extends back to the second dilator 372 forming a loop. In an embodiment, the first dilator 348 and the second dilator 372 are each configured to be coupled to a delivery device to facilitate delivery of the medical assembly 300 including the implant 302 within the patient's body.

In accordance with some embodiments of the invention, the medical assembly 100, 200 or 300 can be coupled to a needle delivery device. In an embodiment, the first dilator 348 and the second dilator 372 can be associated to the needle device before passing through tissue and can be adapted to fit the BSC Advantage, Advantage fit, or Prefyx delivery devices. In an embodiment, the first and second sleeves 304 and 326 are attached to the needle beforehand. In an embodiment, the needle is inserted through the body such as through the skin incision and toward the vagina.

Figure 3I:
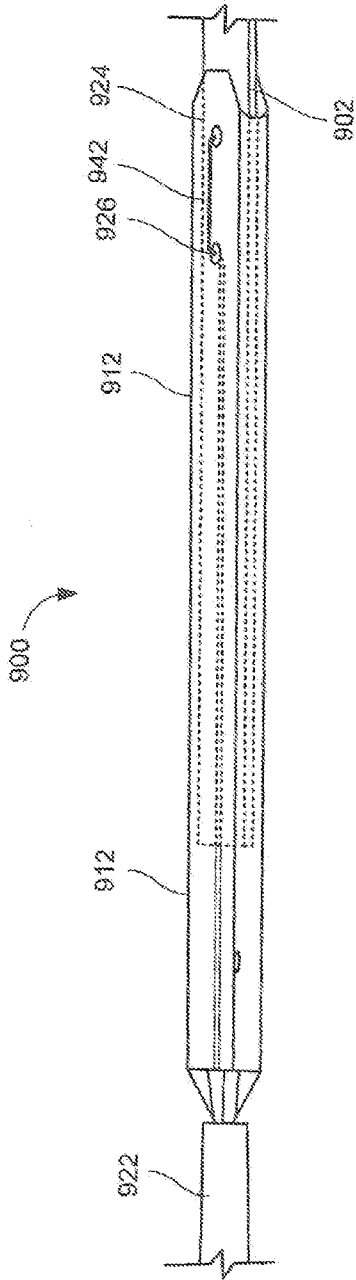
Figure 3J:
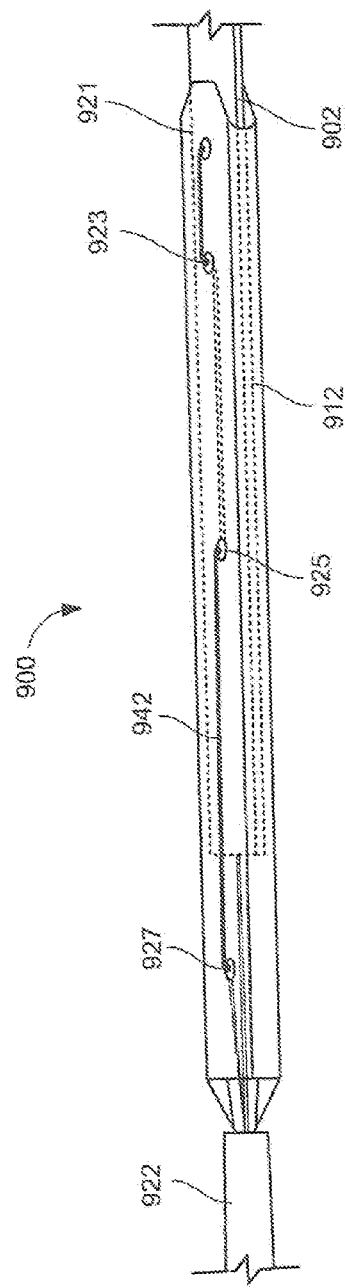

FIGS. 3G-3K illustrate an embodiment of the medical assembly 900 according to an embodiment of the invention. FIG. 3G is a top view of the medical assembly 900. FIG. 3H is a bottom view of the medical assembly 900. FIGS. 3I-3K are perspective views of portions of the medical assembly 900. FIG. 3L is a schematic view of an implant 902 of the medical assembly 900 disposed within a body of a patient.

The medical assembly includes an implant 902, a first sleeve 910, a second sleeve 912, a first dilator 920, and a second dilator 922. In some embodiments, the implant 902 is formed of a mesh material and is configured to be placed into a body of a patient and provide support to a portion of the body of the patient. For example, in some embodiments, the implant 902 is configured to be placed in a pelvic region of a patient and provide support to a pelvic organ, such as a bladder or a bladder neck, of a patient.

A first end portion of the first sleeve 910 is coupled to the implant 902 and a second end portion of the first sleeve 910 is coupled to the dilator 920. Similarly, a first end portion of the second sleeve 912 is coupled to the implant 902 and a second end portion of the sleeve 912 is coupled to the dilator 922. In some embodiments, the sleeves 910 and 912 do not collectively cover the entire length of the implant 902. For example, in some embodiments, the sleeves 910 and 912 collectively cover about 50% of the length of the implant 902. In other embodiments, the sleeves 910 and 912 collectively cover more than 50% of the length of the implant 902. In some embodiments, the sleeves 910 and 912 are configured to help facilitate the movement of the medical assembly 900 within the body of the patient. In some embodiments, the implant 902 includes tangs or tang members along and edge portion. In some embodiments, the tangs or tang members are disposed on the portions of the implant 902 that are within the sleeves 910 and 912.

In the illustrated embodiment, the couplings of the sleeves 910 and 912 to the implant 902 are functional and structurally similar. Accordingly, only the coupling of the second sleeve 912 to the implant 902 will be discussed in detail.

Additionally, in the illustrated embodiment, the couplings of the sleeves 910 and 912 to the dilators 920 and 922 are structurally and functionally similar. Accordingly, only the coupling of the second sleeve 912 to the dilator 922 will be discussed in detail.

As best illustrated in FIG. 3K, the second sleeve 912 defines a cavity or lumen 911 and is coupled to a second end portion 901 of the implant 902. In the illustrated embodiment, a portion of the second end portion 901 of the implant 902 is disposed within the cavity or lumen 911 defined by the second sleeve 912.

The second sleeve 912 is removably coupled to the implant 902 by an elongate member or a suture 942. The suture 942 is coupled to the dilator 922 and extends or is threaded through the implant 902. As best illustrated in FIG. 3G, a top portion or surface 913 of the sleeve 912 defines 4 openings or holes 921, 923, 925, and 927 that communicate with the lumen 911 defined by the second sleeve 912. The suture 942 extends from the dilator 922 into the lumen 911 defined by the sleeve 912 and extends out of the opening 927. The suture 942 then extends along the outer surface 913 of the sleeve 912. The suture 942 then extends into the lumen 911 defined by the sleeve 912 through the opening 925. The suture 942 then extends within the lumen 911 and extends out of the opening 923. The suture 942 then extends along the outer surface 913 of the sleeve 912 and extends into the lumen 911 through the opening 921. The suture 942 then passes through or is woven through the implant 902 and extends from a bottom side of the implant 902.

In some embodiments, the suture 942 is woven through the implant 902 at multiple locations. In other embodiments, the suture 942 passes through the implant 902 one time. In some embodiments, the suture 942 is woven through the implant 902.

As best illustrated in FIG. 3H, a bottom portion or surface 916 of the sleeve 912 defines 2 openings or holes 924 and 926. The suture 942 extends from the lumen 911 of the sleeve 912 via opening 924. The suture 942 then extends along an outer surface of the sleeve 912 and then extends into the lumen 911 via opening 926. The suture 942 then extends towards and is coupled to the dilator 922.

Accordingly, the dilator 922 is coupled to the sleeve 912 and the implant 902 via the suture 942. As described above, the suture 942 forms a loop and is woven or threaded through the implant 902. In the illustrated embodiment, the dilator 922 is also coupled to the sleeve 912 via an additional coupling. For example, in some embodiments, an end portion of the sleeve 912 is tacked or heat welded to the dilator 922. In other embodiments, an adhesive is used to couple the sleeve 912 to the dilator 922.

The medial device also includes an adjustment tab 950. The adjustment tab 950 is coupled to a mid portion of the implant 902 and, as discussed in more detail below, may be used to adjust the position of the implant 902 or the medical device 900 within the body of the patient.

The adjustment tab 950 includes a first end portion 951, a second end portion 953, and a mid-portion 952 disposed between the first end portion 951 and the second end portion 953. In the illustrated embodiment, the first end portion 951 is disposed adjacent to the implant 902. The mid-portion 952 has a width that is smaller than the width of the first end portion 951 and is smaller than then width of the second end portion 953. In some embodiments, the thinner mid-portion 952 of the adjustment tab 950 helps facilitate the cutting of the suture 946 to remove the adjustment tab 950 from the implant 902, as described in more detail below.

An elongate member or suture 946 couples the adjustment tab 950 to the implant 902. In the illustrated embodiment, the suture 946 is threaded or woven through the implant 902 (as best illustrated in FIG. 3G) and forms a loop around the adjustment tab 950 (as best illustrated in FIG. 3K). Specifically, in the illustrated embodiment, the suture 946 extends through openings or lumens 971, 973, 975, and 977 defined by the first end portion 951 and the second end portion 953. In the illustrated embodiment, the second end portion 953 defines a groove 954 that is configured to receive the suture 946. In some embodiments, the suture 946 is coupled to the adjustment tab 950 within the groove 954 such as via an adhesive or a frictional fit. In some embodiments, the suture 946 forms a knot and the knot is frictionally fit within the groove 954 defined by the second end portion 953 of the adjustment tab 950. In some embodiments, the suture 946 may be cut (such as at a location near the mid-portion 952 of the adjustment tab 950) and the adjustment tab 950 can be pulled in a direction away from the implant 902 to remove the adjustment tab 950 and the suture 946 from the implant 902. In such an embodiment, the suture 946 is configured to pass through or be unwoven from the implant 902 in response to the cutting of the suture 946 and the pulling of the adjustment tab 950 in a direction away from the implant 902.

The medical device 900 may be inserted into the body using a variety of different methods. Additionally, the medical device 900 may be placed or inserted into different locations within the body to perform different functions. In some embodiment, the medical device 900 is placed within a pelvic region of the patient and is configured to provide support to a bladder, bladder neck, or urethra of a patient.

In some embodiments, the medical device 900 can be inserted into a body of a patient through a vaginal incision. For example, in some embodiments, the medical device 900 may be placed into the body of the patient using an outside-in procedure. In such embodiments, a delivery device, such as a needle may be inserted into the body such that the needle extends from a skin incision to a vaginal incision, such as an anterior vaginal incision. In embodiments, a curved needle, such as a curved or halo needle as sold by Boston Scientific Corporation may be used. In some embodiments, the delivery device passes though an obturator foramen of the patient as it extends from the skin incision to the vaginal incision.

One end portion of the medical device 900, such as association loop 932, which is coupled to dilator 922, may be coupled to portion of the delivery device that extends from the vaginal incision. The delivery device, which is coupled to the medical device 900, may then be removed or retracted through the skin incision. The medical device 900 then extends from the vaginal incision to the skin incision. The same procedure may be used to place the opposite end portion of the medical device 900 using association loop 930, which is coupled to dilator 920, on the contra lateral side of the urethra. The implant may then be centered or moved such that the implant 902 is disposed below the urethra.

The dilators 920 and 922 and sleeves 910 and 912 may then be removed from the implant 902. For example, the dilator 922 and the sleeve 912 may be removed by cutting the suture 942 and pulling the dilator 922 from the skin incision in a direction away from the body of the patient. In some embodiments, the suture 942 may be cut at a location between openings 927 and 925 (where the suture 942 extends along an outer surface of the sleeve 912. The pulling of the dilator 922 causes the suture to unravel or unweave from the implant 902. Thus, the dilator 922, the sleeve 912 and the suture 942 may be removed leaving the implant 902 in place within the body of the patient. A similar procedure may be used to remove the dilator 920, sleeve 910, and suture 940. FIG. 3L is a schematic illustration of the implant 902 disposed within a body of a patient. The implant 902 is disposed below and is configured to provide support to the urethra UA of the patient. Also, in the illustrated embodiment, the implant 902 extends through the obturator foramens of the patient.

In some embodiments, the adjustment tab 950 may be used to pull or otherwise place the implant 902 into the correct position within the body of the patient. In some embodiments, once the adjustment tab 950 is no longer needed it may be removed from the body of the patient. For example, the suture 946 may be cut and the adjustment tab 950 may be pulled from the body and the implant 902. In some embodiments, the adjustment tab 950 is removed from the body of the patient through the vaginal incision. After the adjustment tab 950 is removed, the vaginal incision may be closed.

In other embodiments, the medical device 900 may be placed using other techniques such as an outside-in technique. For example, in some such embodiments, the medical device 900 may be placed with a delivery device that is coupled to an end portion of the medical device 900 and pushed into place within the body of the patient through a vaginal incision.

FIGS. 4A and 4B illustrate C configuration of a sleeve such as the sleeve 402. In the C configuration, the sleeve 402 encloses the implant 404 in a manner that only a first side 406 (right side), a second side 408 (left side), some portion of a first surface 410 (top surface), a second surface 412 (bottom surface) of the implant 404 are enclosed, whereas some portion of the first surface 410 (top surface) is exposed to bodily tissues and is not shielded within the sleeve 402. The "some portion" can be along half of the width of the sleeves 402, or about half of the width or lesser than half of the width or slightly more than half of the width, and the like as per the requirements.

Figure 4C:
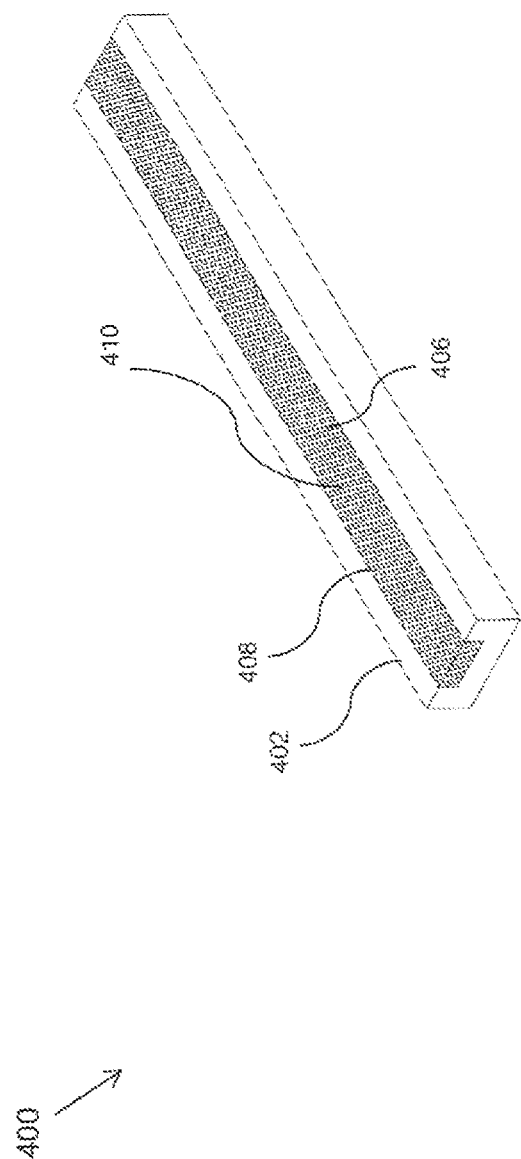

FIGS. 4C and 4D illustrate a U configuration of the sleeve 402. The U configuration encloses only the first side 406, the second side 408, and the second surface 412 (as shown in FIG. 4D), while the first surface 410 (top surface) of the implant 404 is completely exposed to the bodily tissues and not shielded within the sleeve 402. The "some portion" can be along half of the width of the sleeves 402, or about half of the width or lesser than half of the width or slightly more than half of the width, and the like as per the requirements.

Figure 6:
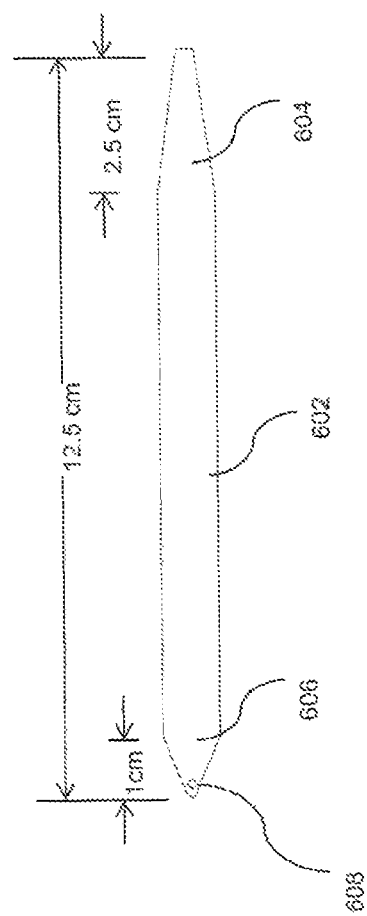
FIG. 6 is perspective view of a sleeve, in accordance with an embodiment of the present invention.

FIG. 6 illustrates an exemplary sleeve with folded ends. The sleeve 602 includes a proximal end portion 604 and a distal end portion 606. In some embodiments, the proximal end portion 604 and the distal end portion 606 of the sleeve 602 can be tapered. The tapered end facilitates withdrawal of the sleeve 602 without disrupting the tissues. The distal end portion 606 of the sleeve 602 may be provided with a hole or opening 608 such that the hole 608 is configured to associate the sleeve 502 with the delivery device. In some embodiments, the distal end portion 606 is associated with one of a dilator, a tube, an association loop and a connector. In an exemplary embodiment, the total length of the sleeve can be 12.5 cm such that the proximal end portion 604 has a length of 2.5 cm whereas the distal end portion 606 has a length of 1.0 cm, as shown in FIG. 6. It must be appreciated that the sleeve 502 can be used in the medical assembly 100 or 200 as described above.

Figure 7:
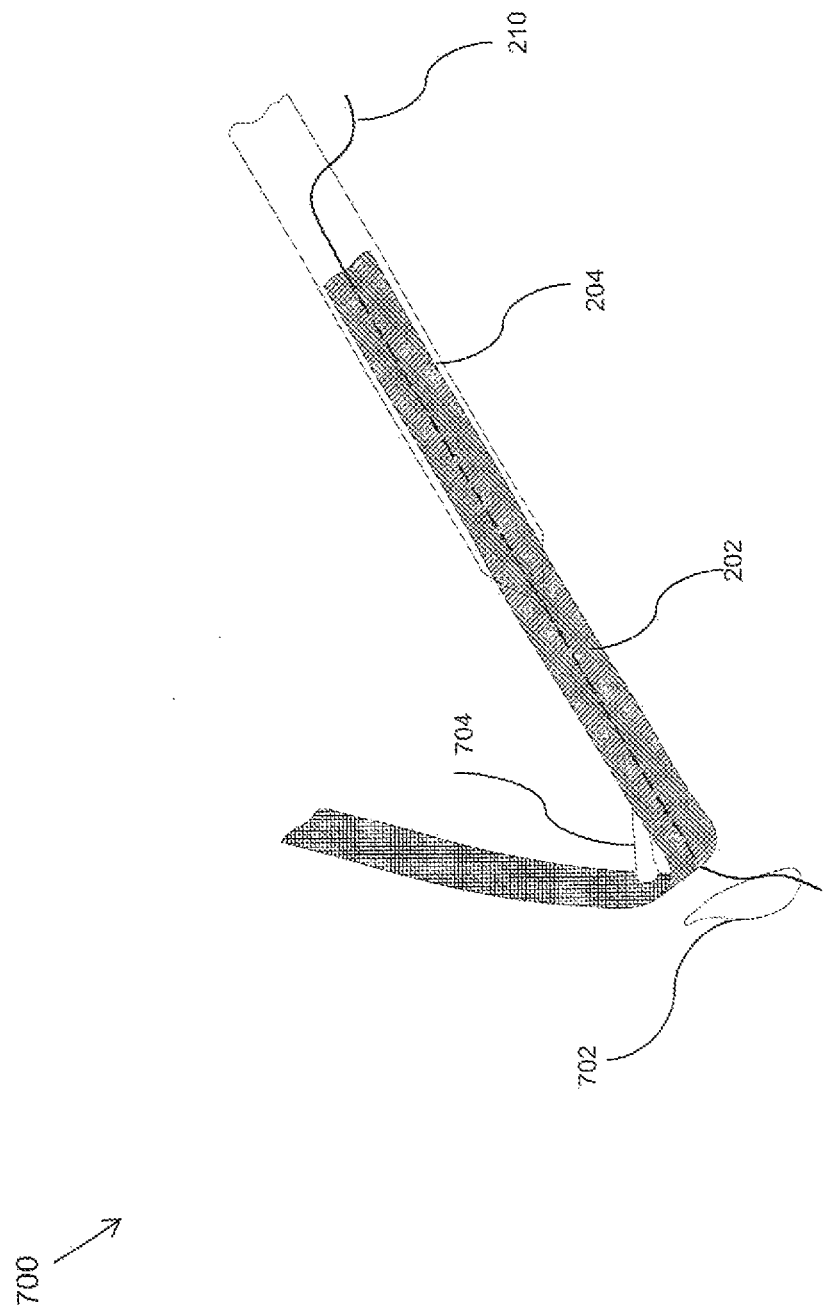
FIG. 7 illustrates delivery of a medical assembly for placement of an implant in a patient's body, in accordance with an embodiment of the present invention.

FIG. 7 illustrates placement of an implant in a patient's body, in accordance with an embodiment of the present invention. The medical assembly 200 is hereafter used for describing placement of the implant such as the implant 202. The implant 202 is inserted inside the body of the patient through a vaginal incision 702 and placed under urethra 704 in a manner that the mid portion 220 of the implant 202 conforms the contour of the urethra 704.

Figure 8:
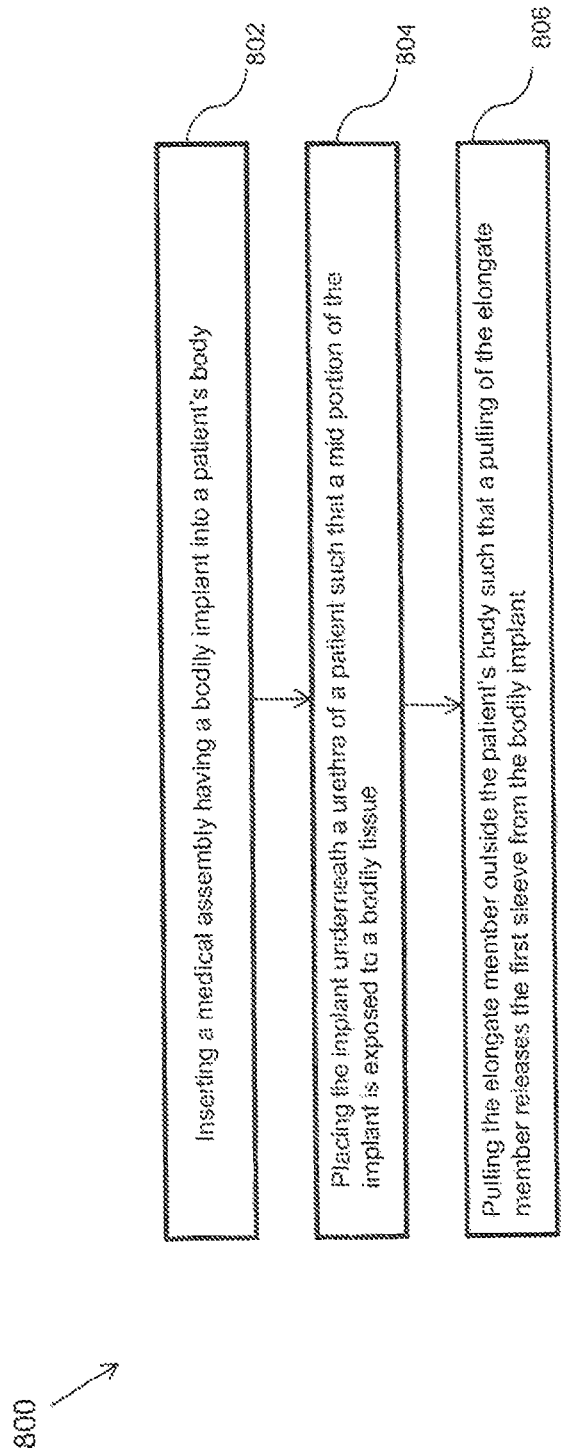
FIG. 8 illustrates a flow chart depicting the method of delivery of a medical assembly, in accordance with various embodiments of the present invention.

FIG. 8 illustrate a flow chart representing a method 800 for the delivery of the medical assembly 200 in a patient's body, in accordance with some embodiments of the present invention. The method 800 includes creating a vaginal incision for inserting the medical assembly 200 inside the patient's body. The medical assembly 200 having the bodily implant 202 can be used to treat incontinence. The medical assembly 200 is inserted into the patient's body at step 802. The bodily implant 202 includes an end portion such that the end portion is enclosed in a sleeve. The sleeve is further coupled to the bodily implant 202 by an elongate member through frictional resistance. In some embodiments, the bodily implant 202 includes a first portion 216 and a second portion 218 such that the first portion and the second portion are enclosed respectively in the first sleeve 204 and the second sleeve 206. The first sleeve 204 and the second sleeve 206 are coupled to the first portion 216 and the second portion 218 of the implant 202 by an elongate member such as the elongate member 280. After inserting the medical assembly 200 inside the patient's body, the implant 202 is placed underneath the urethra of the patient at step 804 such that the mid portion 220 of the implant 202 that is exposed to a bodily tissue contacts the bodily tissue. In accordance with various embodiments, since the first portion 216 and the second portion 218 are covered by the sleeves 204 and 206, therefore, only the mid portion 220 contacts the bodily tissue directly.

In some embodiments, the position of the bodily implant 202 may be adjusted. The bodily implant 202 is adjusted in a manner that the bodily implant 202 contours an outer surface of the urethra that is in contact with the bodily implant 202. The physician may further adjust tension of the implant 202 to readjust the bodily implant 202 to provide it an appropriate tension for effective placement and treatment. The tensioning of the implant 202 may require stretching of the implant 202. The stretch area that is stretched is substantially the mid portion 220 such that when the physician stretches the implant 202, only the mid portion 220 is stretched while the end portions are restricted from stretching because the end portions are covered within the sleeves 204 and 206 while the mid portion 220 is exposed to the bodily tissues. In some embodiments, the end portions may also stretch slightly. As the stretch portion or the mid portion 220 stretches while tensioning of the implant 202, the elongate member 280 shielded within the implant 202 compensates for an additional length required. This may prevent unraveling of the elongate member 280 from the implant 202. In some embodiments, tensioning forces may be transferred from the implant 202 to the sleeves 204 and 206 by the elongate member 280 preventing the stretching of the implant 202 within the sleeves 204 and 206. The interaction of the mid portion 220 of the implant 202 with the bodily tissues underneath the urethra provides the physician with a visual and a tactile feedback through the mid-line or skin incision.

After tensioning the implant 202, the method 800 further includes pulling the elongate member 280 outside the patient's body such that a pulling of the elongate member 280 releases the first and second sleeves 204 and 206 from the bodily implant 202 at step 806. It must be recognized that the elongate member 280 or portions of the elongate member 280 can be removed in a single or different directions through various incisions.

In some embodiments, the loop 260 formed by the elongate member 280 near the mid portion 220 of the implant 202 can be pulled by the physician such that pulling the loop 282 decouples the sleeves 204 and 206 from the implant 202 thereby releasing the first sleeve 204 and the second sleeve 206.

In some embodiments, the loop 282 formed by the elongate member 280 near the mid portion 220 of the implant 202 is cut. Cutting the loop 282 in this manner provides two portions of the elongate member 280 with two free ends such that pulling the two portions of the elongate member 210 separately at the free ends releases the first sleeve 204 and the second sleeve 206. In some embodiments, the first and the second portion of the elongate member 280 can be pulled through the vaginal opening. However, in some embodiments, the first and the second portion of the elongate member 280 can be pulled through groin incisions or through an obturator foreman. In some other embodiments, the first and the second portion of the elongate member 280 can be pulled through the skin incisions.

In accordance with the embodiments described above, the sleeves 204 and 206 are coupled to the implant 202 with the single elongate member 280. In some other embodiments, however, the implant can be coupled to the sleeves 204 and 206 through two elongate members that may be referred to as the first elongate member 210 and the second elongate member 212. In some embodiments, the first elongate member 210 and the second elongate member 212 can further be coupled to the tab 208. The tab 208 can also be coupled to the implant 202 through the third elongate member 214. In some embodiments, the third elongate member 214 can be cut to disassociate the implant 202 from the tab 208. After cutting the third elongate member 214, the tab 208 is pulled through the vaginal opening such that pulling of the tab 208 releases the sleeves 204 and 206 from the bodily implant 202. While the third elongate member 214 is cut, the tab 208 is still coupled to the implant through the first and the second elongate member 210 and 212. Therefore, the pulling of the tab 208 disassociates the first elongate member 210 and the second elongate member 212 thereby removing the first sleeve 204 and the second sleeve 206 from the implant 202. Since the frictional resistance that holds the implant 202 and the sleeves 204 and 206 is easily overcome by the pulling of the tab 208, the sleeves 204 and 206 get decoupled from the implant 202. Also, a small contact surface area between the sleeves 204 and 206 and the implant 202 because the sleeves 204 and 206 cover substantially half of the implant length prevents an alteration of the implant tension caused by pulling of the tab 208.

In some other embodiments, the first elongate member 210 and the second elongate member 212 can be cut just above the tab 208 such that the end portions of the first elongate member 210 and the second elongate member 212 gets free. The physician or the operator can then pull the free ends of the first elongate member 210 and the second elongate member 212 in a direction of the vaginal incision or the skin incisions thereby releasing the first sleeve 204 and the second sleeve 206. In an embodiment, the first sleeve 204 and the second sleeve 206 can be removed or pulled out of the body along with the first elongate member 210 and the second elongate member 212 respectively, through the skin incisions.

In some embodiments, such as those illustrated in FIGS. 3A-3C, the excess slack, for example, at the first portion 336 of the first elongate member 306 can be cut to release the implant 302 from the first sleeve 304 thereby resulting in two free ends of the first elongate member 306. The first dilator 348, external to the body, is pulled in the direction along the vaginal opening or incision. In another embodiment, the first dilator 348 is pulled along and in a direction different from a direction of the vaginal opening or incision. In such examples, the direction of pulling can be along any other bodily opening or a passageway created through incisions along a body portion such as skin incisions, groin incisions, midline incisions, incisions in thigh, buttock or any other bodily location. The dilator 348 is pulled out through the passageway thus created such as through the skin incisions. In an embodiment, the dilator 348 can be pulled out while one end of the first elongate member 306 is still attached to the medical assembly 300. The cut free end of the first elongate member 306 unthreads from the first sleeve 304 and the implant 302. The cut free end of the first elongate member 306 unthreads across holes of the top layer 314 and holes of the bottom layer 316 of the first sleeve 304 thereby decoupling the first sleeve 304 from the implant 302, and removing the first elongate member 306 or the first dilator 348 from the body. The first elongate member 306 travels from the top layer 314 to the bottom layer 316 as the first dilator 348 is pulled. The first sleeve 306 along with the first elongate member 306 is removed as a single part through the passageway that can be the vaginal opening or the skin incision. In an embodiment, the second elongate member 330 can be decoupled from the implant 302 and the second sleeve 326 in a similar manner as described above.

The first sleeve 204 is pulled along with and in a direction of pulling the first elongate member 210 such as through skin incision. In an embodiment, the first elongate member 210 and the first sleeve 204 can be removed without cutting the first sleeve 204. In some embodiments, the second sleeve 206 is pulled along with and in a direction of pulling the second elongate member 212 such as through skin incision. In an embodiment, the second elongate member 212 and the second sleeve 206 can be removed without cutting the second sleeve 206.

Referring again to the medical assembly 200, in some embodiments, the first elongate member 210 and the second elongate member 212 are coupled together separately from the tab 208. In such embodiments, the sleeves 204 and 206 can be decoupled by cutting the first and second elongate members 210 and 212 while the tab 208 still coupled to the implant 202 through the third elongate member 214.

Referring again to the embodiment using a single elongate member, upon separation of the first and second sleeves 204 and 206 from the implant 202, the first sleeve 204 and the second sleeve 206 can be pulled along with the elongate member from the body through skin incisions. In an example, the first sleeve 204 and the second sleeve 206 are pulled out from the patient's body along with the elongate member through two incisions provided in an abdomen or in an obturator area of the patient or through various other skin incisions.

In accordance with some embodiments, the method further includes trimming a portion of the bodily implant 202. The trimmed portion can be tucked to the bodily tissues under skin. In some embodiments, trimming of the implant 202 may not be required as the complete length of the implant 202 acts as a working length. In accordance with various embodiments, the vaginal incision, groin incisions, abdomen incision, or any other skin incision are closed.

It must be appreciated that the above description provides an exemplary treatment procedure, while in some other embodiments; the medical assembly and the method can be used for other treatment purposes such as for various pelvic floor disorders. In accordance with the described embodiments, a transbturator sling or a surgical approach may be utilized.

In some embodiments, a medical assembly includes an implant having a first portion, a second portion and a mid portion between the first portion and the second portion; a first sleeve configured to enclose the first portion of the implant and a second sleeve configured to enclose the second portion of the implant; a tab coupled to the implant; a first elongate member configured to removably couple the implant with the first sleeve, wherein the first elongate member extends from the first portion to the mid portion of the implant and past the mid portion and exits the implant through the mid portion; a second elongate member configured to removably couple the implant with the second sleeve, wherein the second elongate member extends from the second portion to the mid portion of the implant and past the mid portion and exits the implant through the mid portion, wherein the first elongate member and the second elongate member are coupled to the tab and to each other at the tab; and a third elongate member configured to pass through the mid portion of the implant and form a loop configured to couple the mid portion of the implant with the tab.

In some embodiments, the first sleeve and the second sleeve together encloses a maximum of half of a total length of the implant. In some embodiments, the first sleeve and the second sleeve are thin walled flat tubes configured to enclose at least some portion of the implant at ends.

In some embodiments, the device includes a first dilator configured to be coupled to the first sleeve, and a second dilator configured to be coupled to the second sleeve.

In some embodiments, the first elongate member, the second elongate member and the third elongate member include one of a thread, and a medical suture.

In some embodiments, each of the first elongate member and the second elongate member has a single suture running along a portion of length of the implant. In some embodiments, each of the first elongate member and the second elongate member has multiple sutures running along a portion of length of the implant adjacent one another.

In some embodiments, a medical assembly includes an implant having a first portion, a second portion and a mid portion between the first portion and the second portion; a first sleeve configured to enclose the first portion of the implant and a second sleeve configured to enclose the second portion of the implant; and an elongate member configured to removably couple the implant with the first sleeve and the second sleeve, wherein the elongate member is configured to extend from the first portion to the mid portion of the implant and past the mid portion such that the elongate member exits the implant through the mid portion and forms a loop near the mid portion, the elongate member further configured to enter the implant through the mid portion and extend from the mid portion to the second portion of the implant.

In some embodiments, the elongate member is configured to couple the implant with the first sleeve and the second sleeve through frictional resistance. In some embodiments, the first sleeve and the second sleeve together encloses a maximum of half of a total length of the implant.

In some embodiments, the device includes a first dilator configured to be coupled to the first sleeve, and a second dilator configured to be coupled to the second sleeve.

In some embodiments, the first sleeve and the second sleeve are thin walled flat tubes configured to enclose at least a portion of the implant.

In some embodiments, a medical assembly includes an implant having a first portion, a second portion and a mid portion between the first portion and the second portion; a sleeve with a top layer, a bottom layer, and a lumen defined between the top layer and the bottom layer, a first hole provided on the top layer, a second hole provided on the bottom layer, wherein the first hole and the second hole are respectively defined along a thickness of the top layer and the bottom layer; and an elongate member configured to pass through the first hole, along the lumen and the second hole and couple the implant with the sleeve.

In some embodiments, the sleeve is a first sleeve, the medical assembly further including a second sleeve with a top layer, a bottom layer, and a lumen defined between the top layer and the bottom layer, a first hole provided on the top layer, a second hole provided on the bottom layer, wherein the first hole and the second hole are respectively defined along a thickness of the top layer and the bottom layer of the second sleeve.

In some embodiments, the elongate member is a first elongate member, the medical assembly further including a second elongate member configured to pass through the first hole, along the lumen and the second hole and couple the implant with the second sleeve.

In some embodiments, the device includes a tab configured to be coupled with the implant through a third elongate member. In some embodiments, the implant is a mesh based device, the elongate member configured to pass through a mesh cell of the implant. In some embodiments, the implant is a non-mesh based device, the non-mesh based device further including a hole configured to facilitate passing of the elongate member along the implant through the hole. In some embodiments, the elongate member includes a portion laid at a surface external to the top layer or the bottom layer that is configured to provide a slack in the elongate member and configured to facilitate decoupling of the sleeve from the implant.

In some embodiments, a medical assembly includes an implant having a first portion, a second portion and a mid portion between the first portion and the second portion; a first sleeve configured to enclose the first portion of the implant; a first dilator configured to couple with the first sleeve; and a first elongate member configured to couple the first sleeve and the first portion of the implant such that a first portion of the first elongate member extends along the sleeve and lay external to the sleeve while a second portion of the first elongate member extends through a lumen of the first sleeve and across the implant, the first elongate member extending between the first dilator and the first sleeve to form a loop structure of threading.

In some embodiments, the first sleeve includes a top layer, a bottom layer, and a lumen defined between the top layer and the bottom layer, a first hole provided on the top layer, a second hole provided on the bottom layer, wherein the first hole and the second hole are respectively defined along a thickness of the top layer and the bottom layer. In some embodiments, the device includes a second sleeve with a top layer, a bottom layer, and a lumen defined between the top layer and the bottom layer, a first hole provided on the top layer, a second hole provided on the bottom layer, wherein the first hole and the second hole are respectively defined along a thickness of the top layer and the bottom layer of the second sleeve. In some embodiments, the first elongate member extends from the first dilator, across a portion of the first sleeve, along a lumen of the first sleeve, across a portion of the implant and extends back to the first dilator forming the loop. In some embodiments, the first elongate member and the first sleeve are together configured to be pulled out of the body through skin incisions upon implantation of the implant under urethra without cutting the first sleeve. In some embodiments, the assembly includes a second dilator and a second elongate member, wherein the second elongate member extends from the second dilator, across a portion of the second sleeve, along a lumen of the second sleeve, across a portion of the implant and extends back to the second dilator forming a loop. In some embodiments, the first dilator and the second dilator are each configured to be coupled to a delivery device to facilitate delivery of the medical assembly including the implant within the patient's body. In some embodiments, the second elongate member and the second sleeve are together configured to be pulled out of the body through skin incisions upon implantation of the implant under urethra without cutting the second sleeve. In some embodiments, the first elongate member extends along an entire lumen defined by the first dilator such that a portion of the first elongate member stay outside the lumen, the portion staying outside being configured to be pulled by an operator to remove the elongate member from the body.

In some embodiments, a method for placing an implant for the treatment of urinary incontinence in a patient's body, the method includes inserting a medical assembly having a bodily implant into a patient's body such that a first end portion and a second end portion of the bodily implant are enclosed in a first sleeve and a second sleeve respectively, the first sleeve being coupled to the implant by an elongate member through frictional resistance; placing the implant underneath a urethra of a patient such that a mid portion of the implant is exposed to a bodily tissue; and pulling the elongate member outside the patient's body such that a pulling of the elongate member releases the first sleeve from the bodily implant.

In some embodiments, the method includes creating a vaginal incision for inserting the medical assembly inside the patient's body. In some embodiments, the method includes adjusting the position of the bodily implant such that the bodily implant contours an outer surface of the bodily tissue that is in contact with the bodily implant. In some embodiments, the method includes adjusting tension and position of the implant based on a tactile and a visual feedback. In some embodiments, the method includes trimming a portion of the bodily implant.

In some embodiments, the elongate member is configured to couple the second sleeve with the second end portion, and the pulling of the elongate member is configured to release the second sleeve from the bodily implant and; remove the second sleeve along with the elongate member from the body through skin incisions.

In some embodiments, the elongate member is a first elongate member, the medical assembly further includes a second elongate member coupling the second sleeve with the second end portion of the implant, the method includes pulling the second elongate member along with the second sleeve through skin incisions.

In some embodiments, the method includes closing the vaginal incision and the skin incisions.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

What is claimed is:

1. A medical assembly comprising:
    an implant having a first portion, a second portion and a mid portion between the first portion and the second portion;
    a first sleeve configured to enclose the first portion of the implant and a second sleeve configured to enclose the second portion of the implant;
    a tab coupled to the implant;
    a first elongate member configured to removably couple the implant with the first sleeve, wherein the first elongate member extends from the first portion to the mid portion of the implant and past the mid portion and exits the implant through the mid portion;
    a second elongate member configured to removably couple the implant with the second sleeve, wherein the second elongate member extends from the second portion to the mid portion of the implant and past the mid portion and exits the implant through the mid portion;
    wherein the first elongate member and the second elongate member are coupled to the tab and to each other at the tab; and
    a third elongate member configured to pass through the mid portion of the implant and form a loop configured to couple the mid portion of the implant with the tab.

2. The medical assembly of claim 1, wherein the first sleeve and the second sleeve together encloses a maximum of half of a total length of the implant.

3. The medical assembly of claim 1, wherein the first sleeve and the second sleeve are thin walled flat tubes configured to enclose at least some portion of the implant at ends.

4. The medical assembly of claim 1 further comprising a first dilator configured to be coupled to the first sleeve, and a second dilator configured to be coupled to the second sleeve.

5. The medical assembly of claim 1, wherein the first elongate member, the second elongate member and the third elongate member include one of a thread, and a medical suture.

6. The medical assembly of claim 1, wherein each of the first elongate member and the second elongate member has a single suture running along a portion of length of the implant.

7. The medical assembly of claim 1, wherein each of the first elongate member and the second elongate member has multiple sutures running along a portion of length of the implant adjacent one another.

8. A medical assembly comprising:
    an implant having a first portion, a second portion and a mid portion between the first portion and the second portion;
    a first sleeve configured to enclose the first portion of the implant and a second sleeve configured to enclose the second portion of the implant; and
    an elongate member configured to removably couple the implant with the first sleeve and the second sleeve,
    wherein the elongate member is configured to extend from the first portion to the mid portion of the implant and past the mid portion such that the elongate member exits the implant through the mid portion and forms a loop near the mid portion, the elongate member further configured to enter the implant through the mid portion and extend from the mid portion to the second portion of the implant, the elongate member including a first free end and a second free end such that pulling on either the first free end or the second free end decouples the first sleeve and the second sleeve from the implant.

9. The medical assembly of claim 8, wherein the implant is coupled to both the first sleeve and the second sleeve via the elongate member which is a single elongate member.

10. The medical assembly of claim 8, wherein the first sleeve and the second sleeve together encloses a maximum of half of a total length of the implant.

11. The medical assembly of claim 8, further comprising a first dilator configured to be coupled to the first sleeve, and a second dilator configured to be coupled to the second sleeve.

12. The medical assembly of claim 8, wherein the first sleeve and the second sleeve are thin walled flat tubes configured to enclose at least a portion of the implant.

13. A medical assembly comprising:
an implant having a first portion, a second portion and a mid portion between the first portion and the second portion;
a sleeve with a top layer, a bottom layer, and a lumen defined between the top layer and the bottom layer, a first hole provided on the top layer, a second hole provided on the bottom layer, wherein the first hole and the second hole are respectively defined along a thickness of the top layer and the bottom layer;
an elongate member configured to pass through the first hole, along the lumen and the second hole and couple the implant with the sleeve; and
a tab configured to be coupled to the implant, the tab including a first end portion, a mid portion, and a second end portion, the mid portion having a width smaller than a width of the first end portion, the width of the mid portion being smaller than a width of the second end portion.

14. The medical assembly of claim 13, wherein the sleeve is a first sleeve, the medical assembly further including a second sleeve with a top layer, a bottom layer, and a lumen defined between the top layer and the bottom layer, a first hole provided on the top layer, a second hole provided on the bottom layer, wherein the first hole and the second hole are respectively defined along a thickness of the top layer and the bottom layer of the second sleeve.

15. The medical assembly of claim 14, wherein the elongate member is a first elongate member, the medical assembly further including a second elongate member configured to pass through the first hole, along the lumen and the second hole and couple the implant with the second sleeve.

16. The medical assembly of claim 14, wherein the tab is configured to be coupled with the implant through a third elongate member.

17. The medical assembly of claim 13, wherein the implant is a mesh based device, the elongate member configured to pass through a mesh cell of the implant.

18. The medical assembly of claim 13, wherein the implant is a non-mesh based device, the non-mesh based device further including a hole configured to facilitate passing of the elongate member along the implant through the hole.

19. The medical assembly of claim 13, wherein the elongate member includes a portion laid at a surface external to the top layer or the bottom layer that is configured to provide a slack in the elongate member and configured to facilitate decoupling of the sleeve from the implant.

* * * * *